(12) United States Patent
Accetta et al.

(10) Patent No.: US 11,332,468 B2
(45) Date of Patent: May 17, 2022

(54) AZAINDOLE DERIVATIVES AS RHO-KINASE INHIBITORS

(71) Applicant: CHIESI FARMACEUTICI S.p.A., Parma (IT)

(72) Inventors: Alessandro Accetta, Parma (IT); Fabio Rancati, Parma (IT); Christine Edwards, Parma (IT); Andrea Nuzzi, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 154 days.

(21) Appl. No.: 16/954,977

(22) PCT Filed: Dec. 14, 2018

(86) PCT No.: PCT/EP2018/084998
§ 371 (c)(1),
(2) Date: Jun. 17, 2020

(87) PCT Pub. No.: WO2019/121406
PCT Pub. Date: Jun. 27, 2019

(65) Prior Publication Data
US 2020/0392133 A1    Dec. 17, 2020

(30) Foreign Application Priority Data

Dec. 18, 2017 (EP) ..................... 17208193

(51) Int. Cl.
| | | |
|---|---|---|
| *C07D 471/04* | (2006.01) | |
| *C07D 487/04* | (2006.01) | |
| *C07D 519/00* | (2006.01) | |
| *A61K 9/00* | (2006.01) | |
| *A61K 45/06* | (2006.01) | |

(52) U.S. Cl.
CPC ......... *C07D 471/04* (2013.01); *C07D 487/04* (2013.01); *C07D 519/00* (2013.01); *A61K 9/0075* (2013.01); *A61K 9/0078* (2013.01); *A61K 45/06* (2013.01)

(58) Field of Classification Search
CPC ... C07D 471/04; C07D 487/04; C07D 519/00
USPC .................................................. 514/213.01
See application file for complete search history.

(56) References Cited

U.S. PATENT DOCUMENTS 7,612,092 B2 * 11/2009 Funahashi .......... C07D 215/233
                                                            514/312
2006/0241127 A1    10/2006 Feurer et al.

FOREIGN PATENT DOCUMENTS

| WO | WO 2004/039796 A1 | 5/2004 |
| WO | WO 2006/009889 A1 | 1/2006 |
| WO | WO 2009/079008 A1 | 6/2009 |
| WO | WO 2010/032875 A2 | 3/2010 |
| WO | WO 2012/007539 A1 | 1/2012 |
| WO | WO 2014/032755 A2 | 3/2014 |
| WO | WO 2014/118133 A1 | 8/2014 |
| WO | WO 2018/115383 A1 | 6/2018 |
| WO | WO 2018/138293 A1 | 8/2018 |

OTHER PUBLICATIONS

Duong-Quy S, et al. "Role of Rho-kinase and its inhibitors in pulmonary hypertension." Pharmacol Then 137(3):352-64, Elsevier, Netherlands (2013).
Fernandes LB, et al. "Rho kinase as a therapeutic target in the treatment of asthma and chronic obstructive pulmonary disease." Ther Adv Respir Dis. 1(1):25-33, SAGE Publications, United States (2007).
Gosens, R. et al. "Rho-kinase as a drug target for the treatment of airway hyperresponsiveness in asthma." Mini-Rev. Med. Chem. 6: 339-348, University of Groningen, Netherlands (2006).
International Search Report and Written Opinion for International Application No. PCT/EP2018/084998, European Patent Office, Netherlands, dated Aug. 3, 2019, 8 pages.
Jiang, C. et al. "Fasudil, a rho-kinase inhibitor, attenuates bleomycin-induced pulmonary fibrosis in mice." Int. J. Mol. Sci. 13:8293-8307, MDPI, Switzerland (2012).
Riento, K. et al. "Rocks: multifunctional kinases in cell behaviour." Nat. Rev. Mol. Cell Biol. 4:446-456, Nature Publishing Group, England (2003).

* cited by examiner

*Primary Examiner* — Niloofar Rahmani
(74) *Attorney, Agent, or Firm* — Sterne, Kessler, Goldstein & Fox P.L.L.C.

(57) ABSTRACT

The invention relates to compounds of formula I inhibiting Rho Kinase that are tyrosine analogues derivatives, processes of preparing such compounds, pharmaceutical compositions containing them and therapeutic use thereof. Particularly the compounds of the invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

15 Claims, No Drawings

AZAINDOLE DERIVATIVES AS RHO-KINASE INHIBITORS

FIELD OF THE INVENTION

The present invention relates to compounds inhibiting Rho Kinase (hereinafter ROCK Inhibitors); particularly the invention relates to azaindole derivatives, processes for preparing such compounds, pharmaceutical compositions containing them and therapeutic use thereof.

The compounds of the invention are inhibitors of the activity or function of the ROCK-I and/or ROCK-II isoforms of the Rho-associated coiled-coil forming protein kinase (ROCK).

Therefore, the compounds of the invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

BACKGROUND OF THE INVENTION

Rho-associated coiled-coil forming protein kinase (ROCK) belongs to the AGC (PKA/PKG/PKC) family of serine-threonine kinases. Two human isoforms of ROCK have been described, ROCK-I (also referred to as p160 ROCK or ROKβ) and ROCK-II (ROKα) are approximately 160 kDa proteins containing an N-terminal Ser/Thr kinase domain, followed by a coiled-coil structure, a pleckstrin homology domain, and a cysteine-rich region at the C-terminus (Riento, K.; Ridley, A. J. Rocks: multifunctional kinases in cell behaviour. Nat. Rev. Mol. Cell Biol. 2003, 4, 446-456).

Both ROCK-II and ROCK-I are expressed in many human and rodent tissues including the heart, pancreas, lung, liver, skeletal muscle, kidney and brain (Riento and Ridley, 2003). In patients with pulmonary hypertension, ROCK activity is significantly higher in both lung tissues and circulating neutrophils as compared with controls (Duong-Quy S, Bei Y, Liu Z, Dinh-Xuan A T. Role of Rho-kinase and its inhibitors in pulmonary hypertension. Pharmacol Ther. 2013; 137(3):352-64). A significant correlation was established between neutrophil ROCK activity and the severity and duration of pulmonary hypertension (Duong-Quy et al., 2013).

There is now substantial evidence that ROCK is involved in many of the pathways that contribute to the pathologies associated with several acute and chronic pulmonary diseases, including asthma, COPD, bronchiectasis and ARDS/ALI. Given the biological effect of ROCK, selective inhibitors have the potential to treat a number of pathological mechanisms in respiratory diseases, such as smooth muscle hyper-reactivity, bronchoconstriction, airway inflammation and airway remodeling, neuromodulation and exacerbations due to respiratory tract viral infection (Fernandes L B, Henry P J, Goldie R G. Rho kinase as a therapeutic target in the treatment of asthma and chronic obstructive pulmonary disease. Ther Adv Respir Dis. 2007 October; 1(1):25-33). Indeed the Rho kinase inhibitor Y-27632 causes bronchodilatation and reduces pulmonary eosinophilia trafficking and airways hyperresponsiveness (Gosens, R.; Schaafsma, D.; Nelemans, S. A.; Halayko, A. J. Rhokinase as a drug target for the treatment of airway hyperresponsiveness in asthma. Mini-Rev. Med. Chem. 2006, 6, 339-348). Pulmonary ROCK activation has been demonstrated in humans with idiopathic pulmonary fibrosis (IPF) and in animal models of this disease. ROCK inhibitors can prevent fibrosis in these models, and more importantly, induce the regression of already established fibrosis, thus indicating ROCK inhibitors as potential powerful pharmacological agents to halt progression of pulmonary fibrosis (Jiang, C.; Huang, H.; Liu, J.; Wang, Y.; Lu, Z.; Xu, Z. Fasudil, a rho-kinase inhibitor, attenuates bleomycin-induced pulmonary fibrosis in mice. Int. J. Mol. Sci. 2012, 13, 8293-8307).

Various compounds have been described in the literature as Rho Kinase Inhibitors. See e.g. WO2004/039796; WO2006/009889; WO2010/032875; WO2009/079008; WO2014/118133, and from the same Applicant WO 2018/115383 and WO 2018/138293.

There remains a potential for developing novel and pharmacologically improved ROCK inhibitors in many therapeutic areas such as: cardiovascular and respiratory diseases, erectile dysfunction, fibrotic diseases, insulin resistance, kidney failure, central nervous system disorders, auto-immune diseases and oncology.

In view of the number of pathological responses which are mediated by ROCK enzymes, there is a continuing need for inhibitors of such enzymes which can be useful in the treatment of many disorders. The present invention relates to novel compounds which are inhibitors of ROCK-I and ROCK-II isoforms of the Rho-associated coiled-coil forming protein kinase (ROCK), as demonstrated by the pharmacological activity data reported. Furthermore the compounds of the invention have therapeutically desirable characteristics, that makes them particularly suitable to be administered also by inhalation for the treatment of respiratory disease. The compounds of the invention are particularly promising for some pulmonary diseases including asthma, chronic obstructive pulmonary disease (COPD), idiopathic pulmonary fibrosis (IPF) and pulmonary hypertension (PH) and specifically pulmonary arterial hypertension (PAH).

SUMMARY OF THE INVENTION

The present invention is directed to compounds of formula (I)

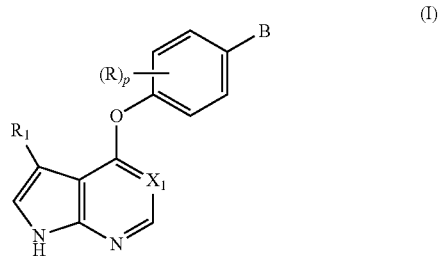

Wherein $X_1$, R, $R_1$, B and p, are as reported below in the detailed description of the invention, acting as ROCK inhibitors, to processes for the preparation thereof, pharmaceutical compositions comprising them either alone or in combination with one or more active ingredient, in admixture with one or more pharmaceutically acceptable carrier.

In one aspect the present invention provides the use of a compound of the invention for the manufacture of a medicament.

In a further aspect the present invention provides the use of a compound of the invention for the preparation of a medicament for the treatment of any disease characterized by ROCK enzyme aberrant activity and/or wherein an inhibition of activity is desirable and in particular through the selective inhibition of the ROCK enzyme isoforms over other Kinases.

Moreover the invention provides a method for prevention and/or treatment of any disease wherein a ROCK enzyme inhibition is desirable, said method comprises administering to a patient in need of such treatment a therapeutically effective amount of a compound of formula (I).

In particular the compounds of the invention alone or combined with other active ingredients may be administered for the prevention and/or treatment of a pulmonary disease including asthma, chronic obstructive pulmonary disease (COPD), idiopathic pulmonary fibrosis (IPF) and pulmonary hypertension (PH) and specifically pulmonary arterial hypertension (PAH).

DETAILED DESCRIPTION OF THE INVENTION

The invention is directed to a class of compounds acting as inhibitors of the Rho Kinase (ROCK).

Said class of compounds inhibits the activity or function of the ROCK enzyme and more specifically, they are inhibitors of ROCK-I and ROCK-II isoforms of the Rho-associated coiled-coil forming protein kinase (ROCK). The invention relates to compounds of formula (I)

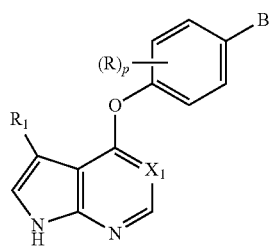

(I)

wherein
$X_1$ is a carbon or a nitrogen atom,
p is zero or an integer from 1 to 3
each R, when present, is H or halogen;
$R_1$ is —H, —CN or $(C_1-C_6)$ alkyl,
B is a nitrogen containing $(C_3-C_8)$heterocycloalkyl,
or
B is a group of formula $R_2R_3N$—$(C_1-C_6)$ alkyl, optionally substituted by one or more substituents selected from hydroxyl, $(C_1-C_6)$ alkyl, $(C_1-C_6)$ hydroxyalkyl, $(C_1-C_6)$ alkoxycarbonyl, $(C_3-C_{10})$ cycloalkoxycarbonyl, aryl $(C_1-C_6)$ alkoxycarbonyl;
wherein
$R_2$ and $R_3$, the same or different, are selected from the group consisting of
—H,
$(C_1-C_6)$ alkyl,
$(C_1-C_6)$ hydroxyalkyl,
$(C_3-C_8)$heterocycloalkyl, further optionally substituted by one or more $(C_1-C_6)$ alkyl; or
B is a group of formula $R_2R_3N$—$(C_1-C_6)$ alkyl, optionally substituted by one or more substituents selected from hydroxyl, $(C_1-C_6)$ alkyl, $(C_1-C_6)$ hydroxyalkyl, $(C_1-C_6)$ alkoxycarbonyl, $(C_3-C_{10})$ cycloalkoxycarbonyl, aryl $(C_1-C_6)$ alkoxycarbonyl; wherein $R_2$ and $R_3$, taken together with the nitrogen atom they are linked to, form a heterocyclic ring, preferably a 4 to 6 membered mono-cyclic saturated heterocyclic ring, wherein at least one further ring carbon atom is optionally replaced by at least one further group independently selected from N, NH, S or O and/or may bear an -oxo (=O) substituent group, said heterocyclic ring is further optionally including spiro disubstitution; and said heterocyclic ring in its turn is further optionally substituted by one or more substituents selected from hydroxyl, $(C_1-C_6)$ alkyl, $(C_1-C_6)$ hydroxyalkyl, $(C_1-C_6)$ alkoxycarbonyl, $(C_3-C_{10})$ cycloalkoxycarbonyl, Aryl $(C_1-C_6)$ alkoxycarbonyl;
or
B is a group of formula $R_2R_3N$—$(C_1-C_6)$ alkyl, optionally substituted by one or more substituents selected from hydroxyl, $(C_1-C_6)$ alkyl, $(C_1-C_6)$ hydroxyalkyl, $(C_1-C_6)$ alkoxycarbonyl, $(C_3-C_{10})$ cycloalkoxycarbonyl, aryl $(C_1-C_6)$ alkoxycarbonyl;
wherein
$R_3$ is selected from the group consisting of
—H,
$(C_1-C_6)$ alkyl,
$(C_1-C_6)$ hydroxyalkyl,
$(C_3-C_8)$heterocycloalkyl, further optionally substituted by one or more $(C_1-C_6)$ alkyl;
$R_2$ is a divalent group —$(CH_2)_q$—, wherein q is an integer from 1 to 3; said divalent group being connected to the carbon atom in ortho position on the adjacent phenyl ring to form a heterocyclic ring, preferably a 4 to 10 membered heterocyclic ring fused with the phenyl ring; said heterocyclic ring being optionally in its turn further substituted with one or more group selected from $(C_1-C_6)$ alkyl, $(C_1-C_6)$ hydroxyalkyl;
or
B is a divalent group —$(CH_2)_s$—, wherein s is an integer from 2 to 8, said divalent group being connected to the adjacent carbon in ortho position on the phenyl ring to form a fused ring; preferably a 4 to 10 membered monocyclic ring fused with the phenyl ring; said ring being further substituted with one or more —$NH_2$;
and pharmaceutically acceptable salts and solvates thereof.

Definitions

The term "pharmaceutically acceptable salts" refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen" or "halogen atoms" includes fluorine, chlorine, bromine, and iodine atom, preferably chlorine or fluorine; meaning Fluoro, Chloro, Bromo, Iodo as substituent.

The term "$(C_1\text{-}C_6)$ alkyl" refers to straight-chained or branched alkyl groups wherein the number of carbon atoms is in the range 1 to 6. Particular alkyl groups are methyl, ethyl, n-propyl, isopropyl and t-butyl.

The expressions "$(C_1\text{-}C_6)$ haloalkyl" refer to the above defined "$(C_1\text{-}C_6)$alkyl" groups wherein one or more hydrogen atoms are replaced by one or more halogen atoms, which can be the same or different.

Examples of said $(C_1\text{-}C_6)$ haloalkyl groups may thus include halogenated, poly-halogenated and fully halogenated alkyl groups wherein all of the hydrogen atoms are replaced by halogen atoms, e.g. trifluoromethyl or difluoro methyl groups.

By way of analogy, the terms "$(C_1\text{-}C_6)$ hydroxyalkyl" or "$(C_1\text{-}C_6)$ aminoalkyl" refer to the above defined "$(C_1\text{-}C_6)$ alkyl" groups wherein one or more hydrogen atoms are replaced by one or more hydroxy (OH) or amino group respectively. Examples include respectively hydroxymethyl, aminomethyl, dimethylaminopropyl and the like.

In the present description, unless otherwise provided, the definition of aminoalkyl encompasses alkyl groups (i.e. "$(C_1\text{-}C_6)$ alkyl" groups) substituted by one or more amino group ($NR_2R_3$). Thus, an example of aminoalkyl is a monoaminoalkyl group such as $R_2R_3N\text{—}(C_1\text{-}C_6)$ alkyl.

With reference to the substituent $R_2$ and $R_3$ as defined above and below, when $R_2$ and $R_3$ are taken together with the nitrogen atom they are linked to form a 4 to 6 membered heterocyclic radical, at least one further ring carbon atom in the said heterocyclic radical is optionally replaced by at least one group selected from N, NH, S O and/or may bear -oxo (=O) substituent groups. It is understood that the said heterocyclic radical might be further optionally substituted on any available position in the ring, namely on a carbon atom, or on any heteroatom available for substitution. Substitution on a carbon atom includes spiro disubstitution as well as substitution on two adjacent carbon atoms, in both cases thus form an additional 5 to 6 membered heterocyclic ring. Examples of said heterocycle radicals are 1-pyrrolidinyl, 1-piperidinyl, 1-piperazinyl, 4-morpholinyl, piperazin-4yl-2-one, 4-methylpiperazine-1-yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, (3aR,6aS)-5-methyl-octahydropyrrolo[3,4-c]pyrrol-2-yl, 8-methyl-2,8-diazaspiro[4.5]decane-2-yl, 5-methyloctahydropyrrolo[3,4-c]pyrrole-2-yl, 1,1-dioxidothiomorpholin-4yl.

The term "$(C_3\text{-}C_{10})$ cycloalkyl" likewise "$(C_3\text{-}C_6)$ cycloalkyl" refers to saturated cyclic hydrocarbon groups containing the indicated number of ring carbon atoms. Examples include cyclopropyl, cyclobutyl, cyclopentyl, cyclohexyl, cycloheptyl, and polycyclic ring systems such as adamantan-yl.

The term "$(C_2\text{-}C_6)$ alkenyl" refers to straight or branched carbon chains with one or more double bonds, conjugated or not conjugated, in cis or trans configuration, wherein the number atoms is in the range 2 to 6.

By way of analogy, the terms "$(C_5\text{-}C_7)$ cycloalkenyl" refers to cyclic hydrocarbon groups containing from 5 to 7 ring carbon atoms and one or two double bonds.

The term "$(C_2\text{-}C_6)$ alkynyl" refers to straight or branched carbon chains with one or more triple bonds wherein the number atoms is in the range 2 to 6.

The term "$(C_2\text{-}C_6)$ hydroxyalkynyl" refers to the above defined "$(C_1\text{-}C_6)$ alkynyl" groups wherein one or more hydrogen atoms are replaced by one or more hydroxy (OH) group.

The term "$(C_2\text{-}C_6)$ aminoalkynyl" refers to the above defined "$(C_1\text{-}C_6)$ alkynyl" groups wherein one or more hydrogen atoms are replaced by one or more ($\text{—}NR_2R_3$) groups.

The expression "aryl" refers to mono, bi- or tri-cyclic carbon ring systems which have 6 to 20, preferably from 6 to 15 ring atoms, wherein at least one ring is aromatic. The expression "heteroaryl" refers to mono-, i- or tri-cyclic ring systems with 5 to 20, preferably from 5 to 15 ring atoms, in which at least one ring is aromatic and in which at least one ring atom is a heteroatom (e.g. N, S or O).

Examples of suitable aryl or heteroaryl monocyclic ring systems include, for instance, phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl radicals and the like.

Examples of suitable aryl or heteroaryl bicyclic ring systems include naphthalenyl, biphenylenyl, purinyl, pteridinyl, pyrazolopyrimidinyl, benzotriazolyl, benzoimidazole-yl, quinolinyl, isoquinolinyl, indolyl, isoindolyl, benzothiopheneyl, benzodioxinyl, dihydrobenzodioxinyl, indenyl, dihydro-indenyl, dihydrobenzo[1,4]dioxinyl, benzothiazole-2-yl, dihydrobenzodioxepinyl, benzooxazinyl radicals and the like.

Examples of suitable aryl or heteroaryl tricyclic ring systems include fluorenyl radicals as well as benzocondensed derivatives of the aforementioned heteroaryl bicyclic ring systems.

In an analogous manner, the expressions "arylene" and "heteroarylene" refer to divalent groups, such a phenylene, biphenylene and thienylene. Such groups are also commonly named as "arenediyl" or "heteroarenediyl" groups. For example o-phenylene is also named benzene-1,2-diyl. Thienyl-ene is alternatively named thiophenediyl.

The expression "$(C_3\text{-}C_6)$ heterocycloalkyl" refers to saturated or partially unsaturated monocyclic $(C_3\text{-}C_6)$ cycloalkyl groups in which at least one ring carbon atom is replaced by at least one heteroatom (e.g. N, S or O) or may bear an -oxo (=O) substituent group. Said heterocycloalkyl (i.e. heterocyclic radical or group) may be further optionally substituted on the available positions in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring. Examples of $(C_3\text{-}C_6)$ heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are 1-pyrrolidinyl, 1-methyl-2-pyrrolidinyl, 1-piperidinyl, 1-piperazinyl, 4-morpholinyl, piperazin-4yl-2-one, 4-methylpiperazine-1-yl, 1-methylpiperidin-4yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3aR,6aS)-5-methyl-octahydropyrrolo[3,4-c]pyrrol-2-yl.

The term "aryl $(C_1\text{-}C_6)$ alkyl" refers to an aryl ring linked to a straight-chained or branched alkyl groups wherein the number of carbon atoms is from 1 to 6, e.g. phenylmethyl (i.e. benzyl), phenylethyl or phenylpropyl.

Likewise the term "heteroaryl $(C_1-C_6)$ alkyl" refers to an heteroaryl ring linked to a straight-chained or branched alkyl groups wherein the number of carbon atoms is from 1 to 6, e.g. furanylmethyl.

The term "alkanoyl", refers to HC(O)— or to alkylcarbonyl groups (e.g. $(C_1-C_6)$alkylC(O)— wherein the group "alkyl" has the meaning above defined. Examples include formyl, acetyl, propanoyl, butanoyl.

Likewise "$(C_1-C_6)$alkyl-sulfonyl" refers to a "$(C_1-C_6)$ alkyl-S(O)$_2$ group wherein alkyl has the meaning above defined. An example is represented by methylsulfonyl.

The term "carbamoyl" refers to amino carbonyl derived groups —C(O)NR$_2$R$_3$, wherein R$_2$ and R$_3$ are as defined above in the definition of aminoalkyl groups and including substituted (preferred aminoalkyl substituted) and spiro substituted derivatives. Examples of such carbamoyl groups include aminocarbonyl, piperazine-1-carbonyl, morpholine-N-carbonyl, morpholine-N-carbonyl, N-(2-(dimethylamino) ethyl)aminocarbonyl, N-(2-(dimethylamino)ethyl)-N-methylaminocarbonyl, N-(3-(dimethylamino)propyl)-N-methylaminocarbonyl, 4-methylpiperazine-1-carbonyl, 4-(dimethylamino)piperidin-1-carbonyl, N-(2-(4-methylpiperazin-1-yl)ethyl)aminocarbonyl, (2-morpholinoethyl) aminocarbonyl, N-methyl-N-(2 morpholino-ethyl) aminocarbonyl, N-(2-(piperidin-1-yl)ethyl)aminocarbonyl, N-methyl-N-(2-(piperidin-1-yl)ethyl)aminocarbonyl, N-(1-methylpiperidin-4-yl-methyl) aminocarbonyl, N-methyl-N-(1-methylpiperidin-4-yl)aminocarbonyl, N-methyl-N-(1-methylpiperidin-4-yl)aminocarbonyl, 5-methyloctahydropyrrolo[3,4-c]pyrrole-2 carbonyl.

The term "hydroxycarbonyl" refers to a terminal group HOC(O)—.

The term "$(C_1-C_{10})$ alkoxy" or "$(C_1-C_{10})$ alkoxyl", likewise "$(C_1-C_6)$ alkoxy" or "$(C_1-C_6)$ alkoxyl" etc., refers to a straight or branched hydrocarbon of the indicated number of carbons, attached to the rest of the molecule through an oxygen bridge. Likewise "$(C_1-C_6)$alkylthio" refers to the above hydrocarbon attached through a sulfur bridge.

The expression "$(C_1-C_6)$ haloalkoxy" or "$(C_1-C_6)$ haloalkoxyl" refers to the above defined haloalkyl, attached through an oxygen bridge, e.g. trifluoromethoxy.

By analogy, the expressions "$(C_3-C_{10})$ cycloalkoxyl" and "$(C_3-C_{10})$ cycloalkyl $(C_1-C_6)$ alkoxyl" refer to cycloalkyl groups attached through an oxygen bridge and chained cycloalkyl-alkoxyl groups respectively. And the expressions "$(C_3-C_6)$ heterocycloalkyloxyl" and "$(C_3-C_6)$ heterocycloalkyl $(C_1-C_6)$ alkoxyl" refer to heterocycloalkyl groups attached through an oxygen bridge and chained heterocycloalkyl-alkoxyl groups respectively. Examples of such $(C_3-C_6)$ heterocycloalkyloxyl and $(C_3-C_6)$ heterocycloalkyl $(C_1-C_6)$ alkoxyl groups are respectively cyclohexyloxyl, cyclohexylmethoxy, (piperidin-4-yl)oxy, 1-methylpiperidin-4-yl)oxy, 2-(piperidin-4-yl)ethoxyl, 2-(1-methylpiperidin-4-yl)ethoxy, and 2-(4-morpholino)ethoxy.

The expressions "Aryloxyl" and "Aryl $(C_1-C_6)$ alkoxyl" likewise "heteroAryloxyl" and "Heteroaryl $(C_1-C_6)$ alkoxyl" refer to Aryl or Heteroaryl groups attached through an oxygen bridge and chained Aryl-alkoxyl or HeteroAryl-alkoxyl groups. Examples of such groups are phenyloxy, benzyloxy and pyridinyloxy respectively.

Likewise, the expressions "$(C_3-C_6)$ heterocycloalkyl-$(C_1-C_6)$ alkyl" and "$(C_3-C_6)$ cycloalkyl-$(C_1-C_6)$ alkyl" refer to the above defined heterocycloalkyl and cycloalkyl groups attached to the rest of the molecule via an alkyl group of the indicated number of carbons. Examples include piperidin-4-yl-methyl and cyclohexylethyl.

The expression "$(C_1-C_6)$ alkoxy-$(C_1-C_6)$ alkyl" refers to the above defined alkoxy group attached to the rest of the molecule via an alkyl group of the indicated number of carbons. Examples include methoxymethyl and methoxypropyl.

The expression "$(C_1-C_6)$ alkoxycarbonyl" refers to the above defined alkoxy group attached to the rest of the molecule via a carbonyl group, e.g. ethoxycarbonyl.

Likewise "$(C_3-C_{10})$ cycloalkoxycarbonyl" and "Aryl $(C_1-C_6)$ alkoxycarbonyl" refers to the above defined "$(C_3-C_{10})$ cycloalkoxyl" and "Aryl $(C_1-C_6)$ alkoxyl" attached to the rest of the molecule via a carbonyl group, e.g. cyclohexyloxylcarbonyl, benzyloxycarbonyl respectively. The expression like "$(C_1-C_6)$ alkoxycarbonyl-amino" refers to the above defined alkoxy group attached to the rest of the molecule via a carbonyl group followed by an amino group (—NR$_2$—), e.g. tert-butoxy-carbonyl-amino-.

"$(C_1-C_6)$ alkoxycarbonyl $(C_3-C_6)$ heterocycloalkyl $(C_1-C_6)$ alkyl" refers to alkoxy carbonyl heterocycloalkyl substituents enchained in the said order and attached to the rest of the molecule via an alkyl group of the indicated number of carbons, e.g. (tert-butyl piperidine-1-carboxylate)-4 yl-methyl.

The expression "$(C_1-C_6)$ aminoalkoxyl" refers to $(C_1-C_6)$ aminoalkyl groups as defined above attached through an oxygen bridge, e.g. (2-(dimethylamino)ethoxy.

The expression "$(C_1-C_6)$ hydroxyalkoxyl" refers to hydroxyalkyl groups as defined above attached to the rest of the molecule through an oxygen bridge, e.g. hydroxyethoxy.

The expression "$(C_1-C_6)$ aminoalkylcarbamoyl" refers to a "carbamoyl" group, as defined above, substituted with a $(C_1-C_6)$ aminoalkyl group (i.e. —C(O)NR$_2$R$_3$ wherein e.g. R$_3$ is an $(C_1-C_6)$ aminoalkyl), e.g. 2(dimethylamino) ethyl carbamoyl.

The term "aryl oxyl $(C_1-C_6)$ alkyl" refers to an aryl-O— wherein aryl has the meaning above defined attached to the rest of the molecule via an alkyl group of the indicated number of carbons, e.g. phenoxyethyl.

The term "aryl alkanoyl" refers to an aryC(O) or arylalkylcarbonyl group [e.g. Aryl($C_1-C_6$)alkylC(O)-] wherein aryl and alkyl have the meaning above defined. Examples are represented by benzoyl, phenylacetyl, phenylpropanoyl or phenylbutanoyl radicals. Likewise "aryl sulfonyl" refers to an arylS(O)$_2$ group wherein aryl has the meaning above defined, e.g. phenylsulfonyl.

Likewise, enchained substituents derive their definition from the composing fragments, like in the above reported definitions, such as "$(C_3-C_6)$ cycloalkyl-carbonyl", "$(C_3-C_6)$ heterocycloalkyl-carbonyl", "heteroaryl-carbonyl"; referring to the above defined fragments attached to the rest of the molecule via a carbonyl group. Examples of such groups include cyclopropanecarbonyl, pyrrolidine-3-carbonyl, (pyridin-3-yl)carbonyl.

The expression "saturated, partially unsaturated or aromatic, five or six membered cycloalkane-diyl, arylene-diyl or heterocycle-diyl" refers to suitable disubstituted cycloalkane or heterocycle or aromatic residue with five or six elements including 1,2-, 1,3- or 1,4-benzene-diyl; 2,3-, 3,4-, 4,5- or 5,6-pyridine-diyl; 3,4-, 4,5- or 5,6-pyridazine-diyl; 4,5- or 5,6-pyrimidine-diyl; 2,3-pyrazinediyl; 2,3-, 3,4- or 4,5-thiophene-diyl/furane-diyl/pyrrole-diyl; 4,5-imidazole-diyl/oxazole-diyl/thiazolediyl; 3,4- or 4,5-pyrazole-diyl/isoxazolediyl/isothiazole-diyl their saturated or partially unsaturated analogues and the like. Other non-vicinal disubstituted residues (diradical) are included too, such as 4,6-pyrimidine-diyl, and the like.

The expression "ring system" refers to mono- or bicyclic or polycyclic ring systems which may be saturated, partially or partially unsaturated or unsaturated, such as aryl, $(C_3-C_{10})$ cycloalkyl, $(C_3-C_6)$heterocycloalkyl or heteroaryl.

The terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 11 membered monocyclic radical, at least one further ring carbon atom in the said heterocyclic radical is optionally replaced by at least one further heteroatom independently selected from N, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Examples of said heterocycle radicals are 1-pyrrolidinyl, 1-piperidinyl, 1-piperazinyl, 4-morpholinyl, piperazin-4-yl-2-one, 4-methylpiperazine-1-yl, 4-metylpiperazine-1-yl-2-one, 7-methyl-2,7-diazaspiro-[3.5]nonan-2-yl, 2-methyl-2,9-diazaspiro[5.5] undecan-9-yl, 9-methyl-3,9-diazaspiro[5.5]-undecan-3-yl, and (3aR,6aS)-5-methyl-octahydropyrrolo[3,4-c]pyrrol-2-yl and the like.

A dash ("-") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

An oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general, the bracketed group is a lateral group, not included into the chain, and brackets are used, when deemed useful, to help disambiguating linear chemical formulas; e.g. the sulfonyl group —SO$_2$— might be also represented as —S(O)$_2$— to disambiguate e.g. with respect to the sulfinic group —S(O)O—.

When a numerical index is used like in the statement "p is zero or an integer from 1 to 3" the statement (value) "p is zero" means that the substituent (R)p is absent, that is to say there is no substituent R on the ring, that is equivalent to say that R, when present, is H.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

It will be apparent that compounds of formula (I) when contain one or more stereogenic center may exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. All such single enantiomers, diastereoisomers and mixtures thereof in any proportion are encompassed within the scope of the present invention. The absolute configuration (R) or (S) for carbon bearing a stereogenic center is assigned on the basis of Cahn-Ingold-Prelog nomenclature rules based on groups' priorities.

The invention further concerns the corresponding deuterated derivatives of compounds of formula (I).

All preferred groups or embodiments described above and herebelow for compounds of formula I may be combined among each other and apply as well mutatis mutandis.

In a preferred embodiment, the invention is directed to compounds of formula (I) as above defined wherein each of $X_1$ is a carbon atom; represented by the formula Ia:

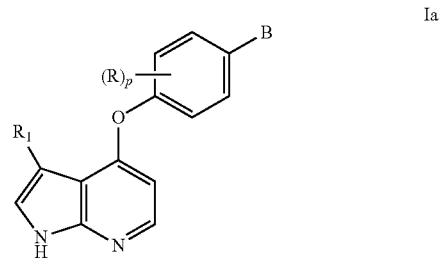

Ia and all the other variables are as defined above.

In a second preferred embodiment, the invention is directed to compounds of formula (I) as above defined wherein $X_1$ is a carbon or a nitrogen atom, p is zero or an integer from 1 or 2, each R, when present, is H or a halogen;

$R_1$ is —H or $(C_1-C_6)$ alkyl,

B is a group $R_2R_3N$—$(C_1-C_6)$ alkyl, said alkyl being optionally substituted by one or more substituents selected from $(C_1-C_6)$ alkyl and/or $(C_1-C_6)$ hydroxyalkyl;

wherein $R_2$ and $R_3$, the same or different, are selected from the group consisting of —H, $(C_1-C_6)$ alkyl, $(C_1-C_6)$ hydroxyalkyl, $(C_3-C_8)$heterocycloalkyl, further optionally substituted by one or more $(C_1-C_6)$ alkyl;

or $R_2$ and $R_3$, taken together with the nitrogen atom they are linked to, form a morpholinyl, 2,7-diazaspiro[4,4] nonan-2-yl or piperazinyl ring further optionally substituted with one or more methyl;

and pharmaceutically acceptable salts and solvates thereof.

In a third preferred embodiment, the invention is directed to compounds of formula (I) as above defined wherein $X_1$ is a ring carbon atom, p is zero or an integer from 1 to 3 each R, when present, is H or a halogen;

$R_1$ is H, —CN or methyl

B is a $(C_3-C_8)$heterocycloalkyl selected from a1, a2 or a3:

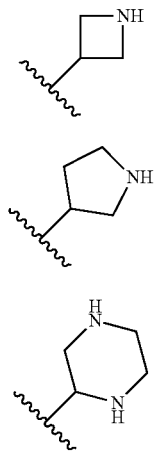

a1 a2 a3 or

B is a group of formula $R_2R_3N$—$(C_1-C_6)$ alkyl, optionally substituted by one or more substituents selected from hydroxyl, $(C_1-C_6)$ alkyl, $(C_1-C_6)$ hydroxyalkyl, $(C_1-C_6)$ alkoxycarbonyl, $(C_3-C_{10})$ cycloalkoxycarbonyl, aryl $(C_1-C_6)$ alkoxycarbonyl;

wherein $R_3$ is selected from the group consisting of
—H,
$(C_1-C_6)$ alkyl,
$(C_1-C_6)$ hydroxyalkyl,
$(C_3-C_8)$heterocycloalkyl, further optionally substituted by one or more $(C_1-C_6)$ alkyl;

$R_2$ is a divalent group —$(CH_2)_q$—, q is an integer from 1 to 3, said divalent group being connected to the carbon atom in ortho position on the adjacent phenyl ring to form a heterobicyclic ring of formula a4, a5, a6, a7 or a8

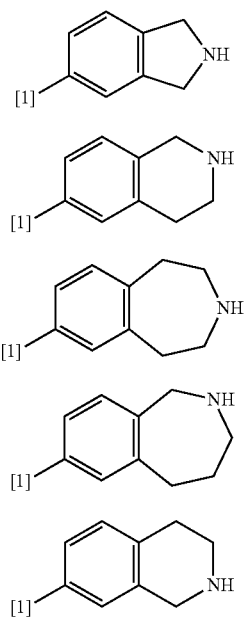

a4 a5 a6 a7 a8 wherein [1] represent the point of attachment of the heterobicyclic ring to the rest of the molecule via the ether bridge, and said heterobicyclic ring being optionally in its turn further substituted with one or more group selected from $(C_1-C_6)$ alkyl and/or $(C_1-C_6)$ hydroxyalkyl;

and pharmaceutically acceptable salts and solvates thereof.

In a fourth preferred embodiment, the invention is directed to compounds of formula (I) as above defined:

wherein $X_1$ is a carbon ring atom, p is zero or an integer from 1 to 3 each R, when present, is H or halogen;

$R_1$ is methyl;

B is a divalent group —$(CH_2)_s$—, wherein s is an integer from 2 to 8, said divalent group being connected to the carbon atom in ortho position of the same phenyl ring to form a bicyclic hydrocarbon ring selected from b1 or b2:

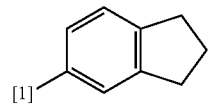

b1

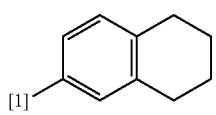

b2 wherein [1] represents the point of attachment of the heterobicyclic ring to the rest of the molecule via the ether bridge, and said bicyclic hydrocarbon ring is further substituted with one or more —$NH_2$;

and pharmaceutically acceptable salts and solvates thereof.

In a further preferred embodiment, the invention is directed to compounds of formula (I) as above defined:

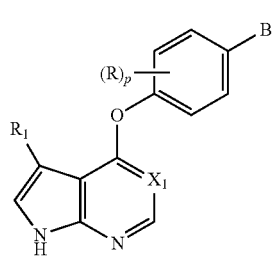

(I)

wherein $X_1$ is a carbon or a nitrogen ring atom, p is zero or an integer from 1 to 3 each R, when present, is fluoro;

$R_1$ is —H, —CN or methyl,

B is azetidinyl (a1), pyrrolidinyl (a2) or piperazinyl (a3) ring;

or

B is a group $R_2R_3N$—$(C_1-C_6)$ alkyl, the —$(C_1-C_6)$ alkyl being optionally substituted by one or more substituents selected from hydroxyl, methyl, hydroxymethyl and cyclopropyl;

wherein

R₂ and R₃, the same or different, are selected from the group consisting of:
—H,
-methyl
-hydroxyethyl
-pyranyl, piperidinyl, further optionally substituted by one or more methyl;
or R₂ and R₃, taken together with the nitrogen atom they are linked to, form a pyrrolidinyl, morpholinyl, 2,7-diazaspiro[4,4]nonan-2-yl or 4-methylpiperazin-1-yl ring,
or R₃ is selected from the group consisting of:
—H,
-methyl;

R₂ is connected to the carbon atom in ortho position on the adjacent phenyl ring to form a heterobicyclic ring selected from 5-methylisoindoline (a4), 6-methyl-1,2,3,4-tetrahydroisoquinoline (a5), 7-methyl-2,3,4,5-tetrahydro-1H-benzo[c]azepine (a6), 7-methyl-2,3,4,5-tetrahydro-1H-benzo[d]azepine (a7) and 7-methyl-1,2,3,4-tetrahydroisoquinoline (a8);

said heterocyclic ring being optionally in its turn further substituted with one or more methyl and/or hydroxymethyl groups;
or B is a bicyclic hydrocarbon ring selected from 2,3-dihydro-1H-indene-5yl (b1) and 1,2,3,4-tetrahydronaphthalene-6yl(b2)

said bicyclic hydrocarbon ring being further optionally in its turn substituted with one or more —NH₂;
and pharmaceutically acceptable salts and solvates thereof.

The invention also provides a pharmaceutical composition comprising a compound of formula I, or a pharmaceutically acceptable salt thereof in admixture with one or more pharmaceutically acceptable carrier or excipient; either alone or in combination with one or more further active ingredient.

In one aspect the invention provides a compound of formula I for use as a medicament.

In a further aspect the invention provides the use of a compound of the invention, or a pharmaceutically acceptable salt thereof, in the manufacture of a medicament for the treatment of disorders associated with ROCK enzymes mechanisms, particularly for the treatment of disorders such as pulmonary diseases.

In particular the invention provides compounds of formula I for use in the prevention and/or treatment of pulmonary disease selected from the group consisting of asthma, chronic obstructive pulmonary disease COPD, idiopathic pulmonary fibrosis (IPF), pulmonary hypertension (PH) and specifically Pulmonary Arterial Hypertension (PAH).

Moreover the invention provides a method for the prevention and/or treatment of disorders associated with ROCK enzymes mechanisms, said method comprising administering to a patient in need of such treatment a therapeutically effective amount of a compound of formula I.

In particular the invention provides methods for the prevention and/or treatment wherein the disorder is asthma, chronic obstructive pulmonary disease (COPD), idiopathic pulmonary fibrosis (IPF), Pulmonary hypertension (PH) and specifically Pulmonary Arterial Hypertension (PAH).

According to specific embodiments, the invention provides the compounds listed in the table 1 below and pharmaceutical acceptable salts thereof.

TABLE 1

| Example No | Stereo-chemistry | Chemical Name |
|---|---|---|
| 1 | | 7-((3-methyl-1H-pyrrolo[2,3-b]pyridin-4-yl)oxy)-1,2,3,4-tetrahydroisoquinoline |
| 2 | | 4-(isoindolin-5-yloxy)-3-methyl-1H-pyrrolo[2,3-b]pyridine |
| 3 | | N-methyl-1-(4-((3-methyl-1H-pyrrolo[2,3-b]pyridin-4-yl)oxy)phenyl)methanamine |
| 4 | | 2-(4-((1H-pyrrolo[2,3-b]pyridin-4-yl)oxy)phenyl)ethanamine |
| 5 | | 7-((3-methyl-1H-pyrrolo[2,3-b]pyridin-4-yl)oxy)-2,3,4,5-tetrahydro-1H-benzo[d]azepine |
| 6 | | 7-((5-methyl-7H-pyrrolo[2,3-d]pyrimidin-4-yl)oxy)-1,2,3,4-tetrahydroisoquinoline |
| 7 | | 5-methyl-4-(4-(pyrrolidin-3-yl)phenoxy)-7H-pyrrolo[2,3-d]pyrimidine |
| 8 | | 2-(4-((5-methyl-7H-pyrrolo[2,3-d]pyrimidin-4-yl)oxy)phenyl)ethanamine |
| 9 | | (4-((5-methyl-7H-pyrrolo[2,3-d]pyrimidin-4-yl)oxy)phenyl)methanamine |
| 10 | | 2-methyl-7-((3-methyl-1H-pyrrolo[2,3-b]pyridin-4-yl)oxy)-1,2,3,4-tetrahydroisoquinoline |
| 11 | | 6-((3-methyl-1H-pyrrolo[2,3-b]pyridin-4-yl)oxy)-1,2,3,4-tetrahydroisoquinoline |
| 12 | | (3-fluoro-4-((3-methyl-1H-pyrrolo[2,3-b]pyridin-4-yl)oxy)phenyl)methanamine |
| 13 | | 3-methyl-4-(4-(piperazin-2-yl)phenoxy)-1H-pyrrolo[2,3-b]pyridine |
| 14 | | 5-((3-methyl-1H-pyrrolo[2,3-b]pyridin-4-yl)oxy)-2,3-dihydro-1H-inden-2-amine |
| 15 | | 7-((3-methyl-1H-pyrrolo[2,3-b]pyridin-4-yl)oxy)-2,3,4,5-tetrahydro-1H-benzo[c]azepine |
| 16 | | 8-((3-methyl-1H-pyrrolo[2,3-b]pyridin-4-yl)oxy)-2,3,4,5-tetrahydro-1H-benzo[c]azepine |
| 17 | | 4-(4-(azetidin-3-yl)phenoxy)-3-methyl-1H-pyrrolo[2,3-b]pyridine |
| 18 | | 3-methyl-4-(4-(pyrrolidin-2-yl)phenoxy)-1H-pyrrolo[2,3-b]pyridine |
| 19 | | 2-(4-((3-methyl-1H-pyrrolo[2,3-b]pyridin-4-yl)oxy)phenyl)ethanamine |
| 20 | | 3-methyl-4-(4-(pyrrolidin-3-yl)phenoxy)-1H-pyrrolo[2,3-b]pyridine |
| 21 | | (4-((3-methyl-1H-pyrrolo[2,3-b]pyridin-4-yl)oxy)phenyl)methanamine |
| 22 | | 3-methyl-4-(4-(2-(pyrrolidin-1-yl)ethyl)phenoxy)-1H-pyrrolo[2,3-b]pyridine |
| 23 | | 1-(3-fluoro-4-((3-methyl-1H-pyrrolo[2,3-b]pyridin-4-yl)oxy)phenyl)ethanamine |
| 24 | | 1-(4-((3-methyl-1H-pyrrolo[2,3-b]pyridin-4-yl)oxy)phenyl)ethanamine |
| 25 | | 2-(4-((3-methyl-1H-pyrrolo[2,3-b]pyridin-4-yl)oxy)phenyl)propan-2-amine |
| 26 | | 6-((3-methyl-1H-pyrrolo[2,3-b]pyridin-4-yl)oxy-1,2,3,4-tetrahydronaphthalen-1-amine |
| 27 | | 4-(4-((3-methyl-1H-pyrrolo[2,3-b]pyridin-4-yl)oxy)benzyl)morpholine |
| 28 | | N-(4-((3-methyl-1H-pyrrolo[2,3-b]pyridin-4-yl)oxy)benzyl)tetrahydro-2H-pyran-4-amine |
| 29 | | N,N-dimethyl-1-(4-((3-methyl-1H-pyrrolo[2,3-b]pyridin-4-yl)oxy)phenyl)methanamine |
| 30 | | 1-methyl-N-(4-((3-methyl-1H-pyrrolo[2,3-b]pyridin-4-yl)oxy)benzyl)piperidin-4-amine |
| 31 | | 2-((4-((3-methyl-1H-pyrrolo[2,3-b]pyridin-4-yl)oxy)benzyl)amino)ethanol |
| 32 | | 4-(4-(2,7-diazaspiro[4.4]nonan-2-ylmethyl)phenoxy)-3-methyl-1H-pyrrolo[2,3-b]pyridine |
| 33 | | 3-methyl-4-(4-((4-methylpiperazin-1-yl)methyl)phenoxy)-1H-pyrrolo[2,3-b]pyridine |
| 34 | | 4-((1,2,3,4-tetrahydroisoquinolin-7-yl)oxy)-1H-pyrrolo[2,3-b]pyridine-3-carbonitrile |
| 35 | | (4-((1H-pyrrolo[2,3-b]pyridin-4-yl)oxy)-3,5-difluorophenyl)methanamine |
| 36 | | (S)-2-amino-3-(3-fluoro-4-((3-methyl-1H-pyrrolo[2,3-b]pyridin-4-yl)oxy)phenyl)propan-1-ol |
| 37 | | (S)-2-amino-3-(4-((3-methyl-1H-pyrrolo[2,3-b]pyridin-4-yl)oxy)phenyl)propan-1-ol |
| 38 | | 2-amino-2-(4-((3-methyl-1H-pyrrolo[2,3-b]pyridin-4-yl)oxy)phenyl)ethanol |

TABLE 1-continued

| Example No | Stereo-chemistry | Chemical Name |
|---|---|---|
| 39 | | (R)-(7-((3-methyl-1H-pyrrolo[2,3-b]pyridin-4-yl)oxy)-1,2,3,4-tetrahydroisoquinolin-3-yl)methanol |
| 18a | First Eluted enantiomer | 3-methyl-4-(4-(pyrrolidin-2-yl)phenoxy)-1H-pyrrolo[2,3-b]pyridine |
| 18b | Second Eluted enantiomer | 3-methyl-4-(4-(pyrrolidin-2-yl)phenoxy)-1H-pyrrolo[2,3-b]pyridine |

The compounds of the invention, including all the compounds here above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be prepared using the processes described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

Thus, processes of preparation described below and reported in the following schemes should not be viewed as limiting the scope of the synthetic methods available for the preparation of the compounds of the invention.

In some cases a step is needed in order to mask or protect sensitive or reactive moieties, generally known protective groups (PG) could be employed, in accordance to general principles of chemistry (Protective group in organic syntheses, 3rd ed. T. W. Greene, P. G. M. Wuts).

The compounds of formula I, including all the compounds here above listed, can be generally prepared according to the procedures shown in the schemes below. Where a specific detail or step differs from the general schemes it has been detailed in the specific examples, and/or in additional schemes.

Compounds of formula I may contain one or more stereogenic centre contained in group B.

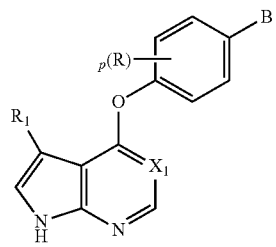

Enantiomerically pure compounds can be prepared according to the reactions described below, by means of enantiomerically pure starting materials and intermediates. Preparation of enantiomerically pure compounds of formula I may be accomplished by means of enantiomerically pure intermediates IV and X as found in the following schemes.

In another approach, enantiomerically pure compounds can be prepared from the corresponding racemates by means of chiral chromatography. Whenever, in compounds of formula I, there are two or more stereogenic centres, the structure is then characterized by different stereoisomers. Stereochemically pure compounds may be obtained by chiral separation from a diastereoisomeric mixture, or stepwise by chromatographic separation of diastereoisomers followed by further chiral separation into single stereoisomers.

Compounds of formula I, wherein B is a nitrogen containing group, may be prepared according to scheme 1 as described hereinafter. The scheme 1 provides at least one non-limiting synthetic route for the preparation of examples 1 to 26 and for example 35.

For synthetic convenience, where group B contains one or more primary or secondary amino moieties, it may require one or more protective groups in order to mask amino group reactivity. A suitable protective group for the amino moiety can be a carbamate such as Boc (tert-butoxycarbonyl), Cbz (benzyloxycarbonyl) or ethyl carbamate. For the sake of clarity, group B, wherein all primary and secondary amino moieties are protected by a carbamate, is represented by the group W Typical groups (PG$_1$) for protection of the NH of the 5-membered ring of the bicyclic intermediate III or VI can be 2-[(trimethylsilyl)ethoxy]methyl (SEM), 4-toluenesulfonyl (Ts) and p-methoxybenzyl (PMB), and anyhow not limiting the use of other protective groups. Intermediate III, wherein PG$_1$ is SEM, may be prepared from the corresponding intermediate II and a suitable reagent such as SEM-Cl ([2-(trimethylsilyl)ethoxy]methyl chloride). Reaction between said components may be carried out in a polar organic solvent such as DMF or DCM, in the presence of a strong base, such as NaH, at RT or lower.

SCHEME 1

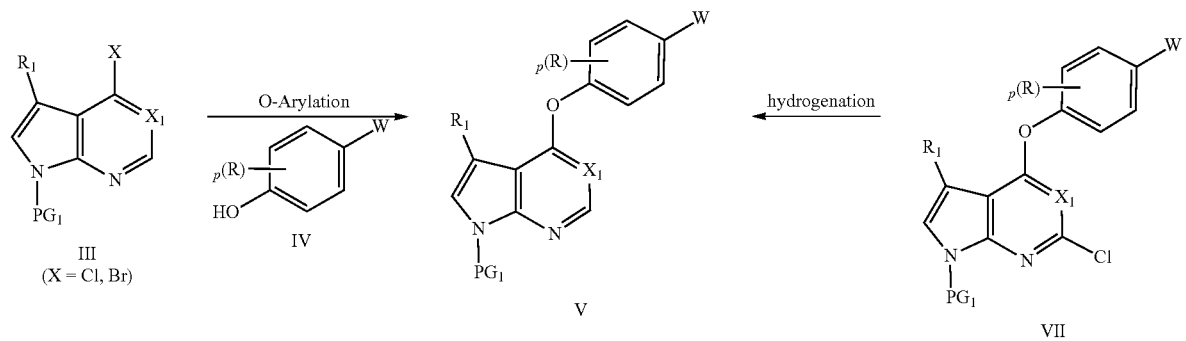

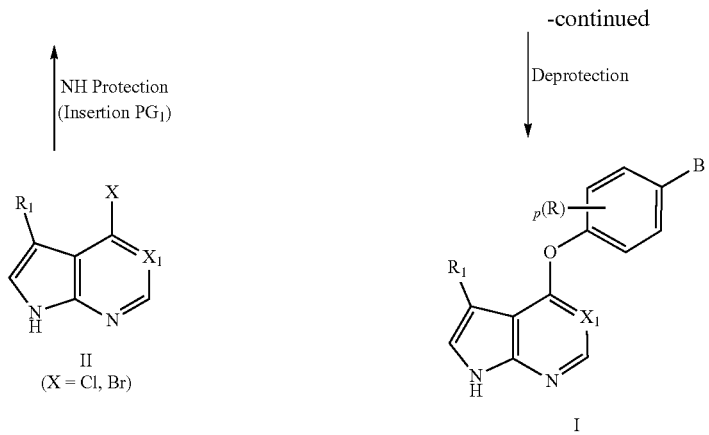

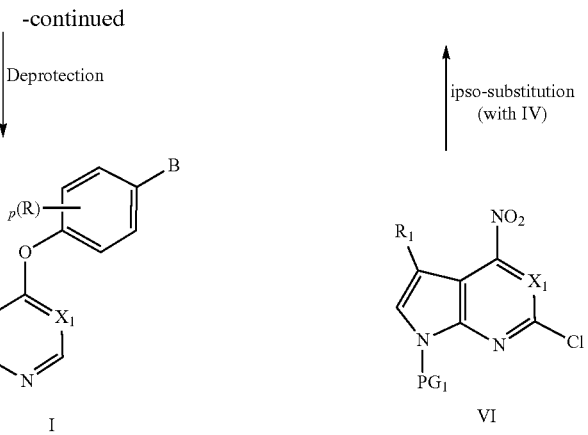

Intermediate V may be obtained from Intermediates III and IV through a palladium catalyzed O-arylation. For example the reaction may be carried out by reacting the aryl halide intermediate III and the phenol derivative IV in a suitable organic solvent such as toluene or THF, in the presence of an inorganic base such as $K_2CO_3$, with a suitable palladium catalytic system such as $Pd_2dba_3$/XPhos or an alternative palladium source/phosphine based ligand at high temperature (around 100° C.) for a time ranging from a few hours to overnight.

In a different approach, intermediate V may be obtained with a two-step synthesis starting from intermediate VI. In the first step ipso-substitution of the nitro group of the intermediate VI by the phenol of intermediate IV gives intermediate VII. The reaction may be carried out in a high boiling organic solvent such as DMSO, at a temperature equal to or higher that 100° C. and in the presence of an inorganic base such as $K_2CO_3$. In the second step intermediate VII can be converted into intermediate V by removing the chlorine atom by means of heterogeneous palladium catalyzed hydrogenation. The reaction can be performed by reacting intermediate VII under a hydrogen atmosphere in the presence of Pd/C and an organic base such as TEA.

Intermediate VI may be prepared similarly to intermediate III from a corresponding unprotected heterocycle as described above for intermediate III.

Removal of all protective groups from intermediate V ($PG_1$ and Boc carbamate contained in W) to give compounds of formula I (wherein B is a nitrogen containing group) may be achieved using generally known methods (Protective group in organic syntheses, $3^{rd}$ ed. T. W. Greene, P. G. M. Wuts). For example, when $PG_1$ is SEM and W contains one or more Boc groups, cleavage may be achieved by an acidic treatment using TFA in an organic solvent such as DCM or inorganic acids in organic solvents such as hydrochloric acid in dioxane. Complete removal of the SEM group may require an extra treatment with a solution of ammonia in methanol or aqueous LiOH.

SCHEME 2

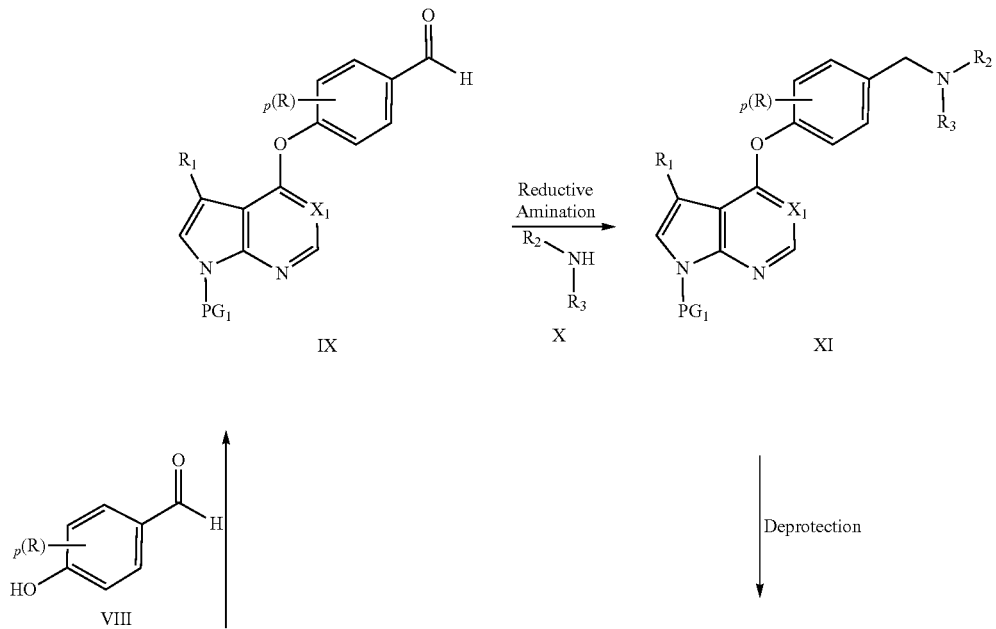

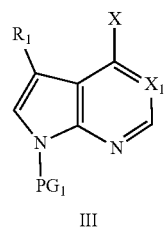

III

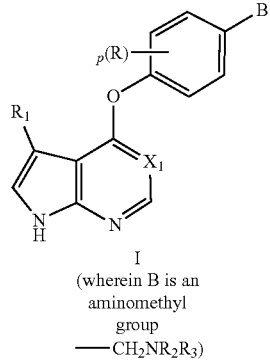

I
(wherein B is an aminomethyl group —CH₂NR₂R₃)

Compounds of formula I, wherein B is an N-substituted aminomethyl group (—CH₂NR₂R₃ with either R₂ or R₃ not equal to H), may be prepared according to scheme 2 that provides at least one non-limiting synthetic route for the preparation of examples 27 to 33.

Intermediate IX may be obtained from intermediate III and intermediate VIII through a palladium catalyzed O-arylation using similar reaction conditions as already reported for obtaining intermediate V from intermediates III and IV.

Intermediate XI may be prepared from intermediate IX by means of a reductive amination with intermediate X. Reductive amination can be performed by reacting aldehyde intermediate IX and a suitable amino intermediate X, using a reducing agent such as NaBH(OAc)₃, NaBH₃CN or NaBH₄ and in a suitable organic solvent such as DCE, DCM, THF or MeOH. The reaction proceeds smoothly at room temperature over a couple of hours. It could be useful to react the amine and the aldehyde to pre-form the imine before adding the reducing agent. Deprotection of intermediate XI to give a compound of formula I (wherein B is an N-substituted aminomethyl group) can be achieved by using the same conditions applied to intermediate V and already described for scheme 1.

SCHEME 3

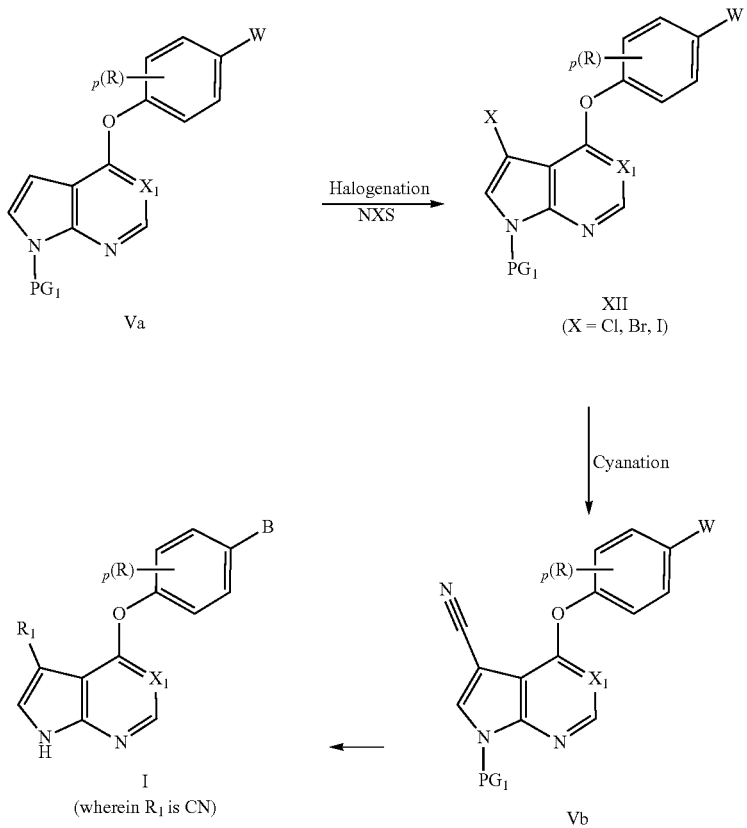

Compounds of formula I where $R_1$ is a cyano group (—CN), may be prepared according scheme 3 that provides at least one non-limiting synthetic route for the preparation of example 34.

Intermediate Va may be converted into the intermediate XII by an electrophilic halogenation with the corresponding NXS (N-halosuccinimide, X: Cl, Br or I) carried out in an organic solvent such as MeCN and at temperature around RT for a few hours.

Intermediate XII can be converted into intermediate Vb by metal catalyzed cyanation. For example, intermediate XII may be reacted with a source of cyanide such as potassium cyanide/18-crown-6 or zinc cyanide in the presence of a Pd catalyst, such as tetrakis(triphenylphosphine)palladium(0) or $Pd_2(dba)_3$ with 1,1'-ferrocenediylbis(diphenylphosphine) and a source of copper (I) such as CuI, in an organic solvent such as DMF, and at a temperature higher than 100° C. for a few hours or longer, to give intermediate Vb. Conversion of intermediate Vb to give compounds of formula I ($R_1$ is CN) can be accomplished as already described for intermediate V in scheme 1.

ethyl) with a reducing agent such as $NaBH_4$, $LiBH_4$, or $LiAlH_4$ in an organic aprotic solvent such as THF or $Et_2O$, by reaction at a temperature higher than RT, for times longer than 24 h. In some cases the reduction may lead to an oxazolidinone ring formed between the newly generated hydroxymethyl group and the carbamate protecting the amino group. In this case, as described for example 39, an additional step of alkaline hydrolysis is needed for example by reaction of the crude with 6N NaOH in a mixture of aqueous/organic solvent such as water/THF, at temperature of 100° C. or higher, for times up to three days.

Deprotection of intermediate Vd (wherein W contains —$CH_2OH$) to give a compound of formula I can be carried out as already described in scheme 1.

The compounds of the invention are inhibitors of kinase activity, in particular Rho-kinase activity. Generally speaking, compounds which are ROCK inhibitors may be useful in the treatment of many disorders associated with ROCK enzymes mechanisms.

SCHEME 4

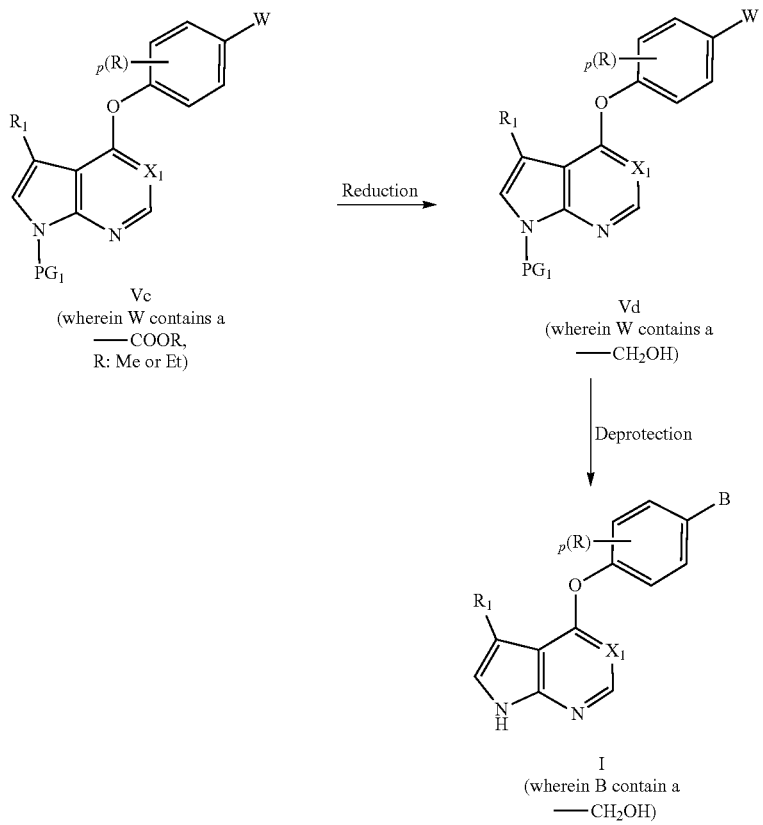

Vc
(wherein W contains a
—COOR,
R: Me or Et)

Vd
(wherein W contains a
—$CH_2OH$)

I
(wherein B contain a
—$CH_2OH$)

A compound of formula I (wherein B contain an hydroxymethyl group) may be prepared according scheme 4. This scheme provides at least one non-limiting synthetic route for the preparation of examples 36 to 39.

Intermediate Vc (wherein W contains a —COOR, R: methyl or ethyl) may be converted by FGI (functional group interconversion) to hydroxymethyl intermediate Vd by reduction of the ester to give the corresponding alcohol. Reduction can be carried out by reacting the ester intermediate Vc (wherein W contains a —COOR, R: methyl or In one embodiment, the disorders that can be treated by the compounds of the invention include glaucoma, inflammatory bowel disease (IBD) and pulmonary diseases selected from asthma, chronic obstructive pulmonary disease (COPD), interstitial lung disease such as idiopathic pulmonary fibrosis (IPF) and pulmonary arterial hypertension (PAH).

In another embodiment, the disorder that can be treated by the compound of the present invention is selected from the group consisting of asthma, chronic obstructive pulmonary disease (COPD) and interstitial lung disease such as idiopathic pulmonary fibrosis (IPF) and pulmonary arterial hypertension (PAH).

In a further embodiment, the disorder is idiopathic pulmonary fibrosis (IPF) or pulmonary arterial hypertension (PAH).

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds of the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination (i.e. as co-therapeutic agents administered in fixed dose combination or in combined therapy of separately formulated active ingredients) with other pharmaceutical active ingredients selected from organic nitrates and NO donors; inhaled NO; stimulator of soluble guanylate cyclase (sGC); prostacyclin analogue PGI2 and agonist of prostacyclin receptors; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors; human neutrophilic elastase inhibitors; compounds inhibiting the signal transduction cascade, such as tyrosine kinase and/or serine/threonine kinase inhibitors; antithrombotic agents, for example platelet aggregation inhibitors, anticoagulants or profibrinolytic substances; active substances for lowering blood pressure, for example calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists; neutral endopeptidase inhibitors; osmotic agents; ENaC blockers; anti-inflammatories including corticosteroids and antagonists of chemokine receptors; bronchodilators for example beta2agonist and muscarinic antagonists; antihistamine drugs; anti-tussive drugs; antibiotics such as macrolide and DNase drug substance and selective cleavage agents such as recombinant human deoxyribonuclease I (rhDNase); agents that inhibit ALK5 and/or ALK4 phosphorylation of Smad2 and Smad3; tryptophan hydroylase 1 (TPH1) inhibitors and multi-kinase inhibitors.

In a preferred embodiment, the compounds of the invention are dosed in combination with phosphodiesterase V such as sildenafil, vardenafil and tadalafil; organic nitrates and NO donors (for example sodium nitroprusside, nitroglycerin, isosorbide mononitrate, isosorbide dinitrate, molsidomine or SIN-1, and inhaled NO); synthetic prostaciclin analogue PGI2 such as iloprost, treprostinil, epoprostenol and beraprost; agonist of prostacyclin receptors such as selexipag and compounds of WO 2012/007539; stimulator of soluble guanylate cyclase (sGC) like riociguat and tyrosine kinase like imatinib, sorafenib and nilotinib and endothelin antagonist (for example macitentan, bosentan, sitaxentan and ambrisentan).

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage comprised between 0.001 and 1000 mg/day, preferably between 0.1 and 500 mg/day.

When the compounds of formula (I) are administered by the inhalation route, they are preferably given at a dosage comprised between 0.001 and 500 mg/day, preferably between 0.1 and 100 mg/day.

A pharmaceutical composition comprising a compound of the invention suitable to be administered by inhalation, such as inhalable powders, propellant-containing metering aerosols or propellant-free inhalable formulations.

The invention is also directed to a device comprising the pharmaceutical composition comprising a compound according to the invention, which may be a single- or multi-dose dry powder inhaler, a metered dose inhaler and a soft mist nebulizer.

The following examples illustrate the invention.

PREPARATIONS OF INTERMEDIATES AND EXAMPLES

General Experimental Details

Purification by chromatography refers to purification using the CombiFlash® Companion purification system or the Biotage SP1 purification system. Where products were purified using an Si cartridge, this refers to an Isolute® pre-packed polypropylene column containing unbounded activated silica with irregular particles with average size of 50 μm and nominal 60 Å porosity. Fractions containing the required product (identified by TLC and/or LCMS analysis) were pooled and concentrated in vacuo. Where an SCX-2 cartridge was used, 'SCX-2 cartridge' refers to an Isolute® pre-packed polypropylene column containing a non-endcapped propylsulphonic acid functionalised silica strong cation exchange sorbent. Where HPLC was used for purification (Purification by MDAP) fractions containing the required product (identified by TLC and/or LCMS analysis) were pooled and the solvent removed using a Biotage EV10 Evaporator. Alternatively the pooled product fraction was lyophilised.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz or on a Bruker Fourier 300 spectrometer with a 5 mm dual probe operating at 300 MHz. Shifts are given in ppm relative to tetramethylsilane.

LC-MS Method 1

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid.

Gradient:

| Gradient-Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 2

Quattro Micro Mass Spectrometer with a C18-reverse-phase column (100×2.1 mm Acquity BEH with 1.7 μm particle size) maintained at 40° C., elution with A: water+0.1% formic acid; B: MeCN+0.1% formic acid.

Gradient:

| Gradient-Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 3

QDa Mass Spectrometer with a C18-reverse-phase column (50×2.1 mm Acquity CSH with 1.7 μm particle size) maintained at 40° C., elution with A: water+0.1% formic acid; B: MeCN+0.1% formic acid.

Gradient:

| Gradient-Time | flow (mL/min) | % A | % B |
| --- | --- | --- | --- |
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

LC-MS Method 4

QDa Mass Spectrometer with a C18-reverse-phase column (50×2.1 mm Acquity BEH with 1.7 μm particle size) maintained at 50° C., elution with A: water+0.1% formic acid; B: MeCN+0.1% formic acid.

Gradient:

| Gradient-Time | flow (mL/min) | % A | % B |
| --- | --- | --- | --- |
| 0.00 | 1 | 97 | 3 |
| 1.50 | 1 | 1 | 99 |

-continued

| Gradient-Time | flow (mL/min) | % A | % B |
|---|---|---|---|
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

LC-MS Method 5

QZ Mass Spectrometer with a C18-reverse-phase column (30×4.6 mm Phenomenex Luna with 3 μm particle size), elution with A: water+0.1% formic acid; B: MeCN+0.1% formic acid.

Gradient:

| Gradient-Time | flow (mL/min) | % A | % B |
|---|---|---|---|
| 0.0 | 2 | 95 | 05 |
| 0.3 | 2 | 95 | 05 |
| 4.3 | 2 | 05 | 95 |
| 5.3 | 2 | 05 | 95 |
| 5.8 | 2 | 95 | 05 |
| 6.0 | 2 | 95 | 05 |

Detection-MS, UV PDA

MS ionisation method-Electrospray (positive/negative ion).

LC-MS Method 6

Waters Platform LC with a C18-reverse-phase column (30×4.6 mm Phenomenex Luna 3 μm particle size), elution with A: water+0.1% formic acid; B: acetonitrile+0.1% formic acid.

Gradient:

| Gradient-Time | flow (mL/min) | % A | % B |
|---|---|---|---|
| 0.00 | 2 | 95 | 5 |
| 0.50 | 2 | 95 | 5 |
| 4.50 | 2 | 5 | 95 |
| 5.50 | 2 | 5 | 95 |
| 6.00 | 2 | 95 | 5 |

Detection-MS, ELS, UV (100 μl split to MS with in-line UV detector)

MS ionisation method-Electrospray (positive and negative ion).

LC-MS Method 7

QDa Mass Spectrometer with a C18-reverse-phase column (50×2.1 mm Acquity CSH with 1.7 μm particle size) maintained at 40° C., elution with A: 95/5 water/acetonitrile+0.05% formic acid; B: 95/5 acetonitrile/water+0.05% formic acid.

Gradient:

| Gradient-Time | flow (mL/min) | % A | % B |
|---|---|---|---|
| 0.00 | 1 | 99 | 1 |
| 1.50 | 1 | 1 | 99 |
| 1.90 | 1 | 1 | 99 |
| 2.00 | 1 | 99 | 1 |

Detection-MS, UV PDA

MS ionisation method-Electrospray (positive/negative ion).

MDAP Method (Acidic)

Agilent Technologies 1260 Infinity purification system with an XSELECT CSH Prep C18 column (19×250 mm, 5 μm OBD) maintained at RT Mobile Phase A: 0.1% aqueous formic acid Mobile Phase B: 0.1% formic acid in acetonitrile Flow Rate: 20 ml/min Gradient Program: 10%-95%, 22 min, centered around a specific focused gradient Sample: Injection of a 20-60 mg/ml solution in DMSO (+optional formic acid and water)

MDAP Method (Basic)

Agilent Technologies 1260 Infinity purification system with an XBridge Prep C18 OBD column (19×250 mm, 5 μm OBD) maintained at RT Mobile Phase A: 0.1% aqueous ammonia Mobile Phase B: 0.1% ammonia in acetonitrile Flow Rate: 20 ml/min Gradient Program: 10%-95%, 22 min, centered around a specific focused gradient Sample: Injection of a 20-60 mg/ml solution in DMSO+ optional formic acid and water)

SFC Methods

Supercritical Fluid Chromatography (SFC) was carried out using either a Waters Thar Prep100 preparative SFC system (P200 $CO_2$ pump, 2545 modifier pump, 2998 UV/VIS detector, 2767 liquid handler with Stacked Injection Module) or a Waters Thar Investigator semi preparative system (Waters Fluid Delivery Module, 2998 UV/VIS detector, Waters Fraction Collection Module). The column and isocratic method used is indicated for each compound and the single enantiomers were analysed using the methods given. Some of the compounds may have gone through a second purification process in order to achieve the required % ee purity.

Abbreviations Used in the Experimental Section:

DCE=1,2-Dichloroethane; DCM=Dichloromethane; DIPEA=Di-isopropylethylamine; DMF=N,N-dimethylformamide; DMSO=Dimethylsulphoxide; h=Hour(s); HATU=(1-[Bis(dimethylamino)methylene]-1H-1,2,3-triazolo[4,5-b]pyridinium 3-oxide hexafluorophosphate); HPLC=High performance liquid chromatography; IMS=Industrial methylated spirits; LCMS=Liquid chromatography-mass spectrometry; MDAP=Mass-directed autopurification; MeCN=Acetonitrile; NIS=N-Iodosuccinimide; $Pd_2(dba)_3$=Tris(dibenzylideneacetone)dipalladium(0); $Pd(PPh_3)_4$Tetrakis(triphenylphosphine)palladium(0); Rt=Retention time; RT=Room temperature; SFC=Supercritical Fluid Chromatography; TFA=Trifluoroacetic acid; THF=Tetrahydrofuran; XPhos=2-Dicyclohexylphosphino-2',4',6'-triisopropylbiphenyl In the procedures that follow, some of the starting materials are identified through an "Intermediate" or "Example" number with indications on step name.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The stereochemistry of the compounds in the Examples, where indicated, has been assigned on the assumption that absolute configuration at resolved stereogenic centers of starting materials is maintained throughout any subsequent reaction conditions.

Example 1

Step A

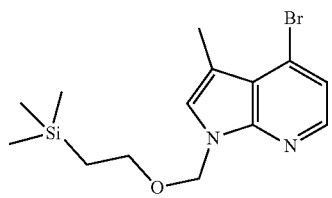 [SMILES: Cc1cn(COCC[Si](C)(C)C)c2nccc(Br)c12]

4-Bromo-3-methyl-1-((2-(trimethylsilyl)ethoxy)methyl)-1H-pyrrolo[2,3-b]pyridine (Intermediate 1A-a)

4-Bromo-3-methyl-7-azaindole (4.0 g, 18.95 mmol) was dissolved in DMF (37 mL) and the solution was cooled in an ice bath. Sodium hydride (60% on mineral oil, 1.14 g, 28.43 mmol) was added and the mixture was stirred under a stream of nitrogen for 1 h. 2-(Trimethylsilyl)ethoxymethyl chloride (4.0 mL, 22.74 mmol) was added dropwise and then the reaction mixture was stirred for a further 30 min. After quenching with water (20 mL), the product was extracted three times into ethyl acetate. The combined extracts were dried ($Na_2SO_4$) and evaporated. The residue was chromatographed on a 120 g Si cartridge eluting with 0-25% ethyl acetate in cyclohexane to give Intermediate 1A-a as a colourless oil (3.78 g).

LCMS (Method 4): Rt=1.90 min. m/z 341.1/343.0 $[M+H]^+$

Step B

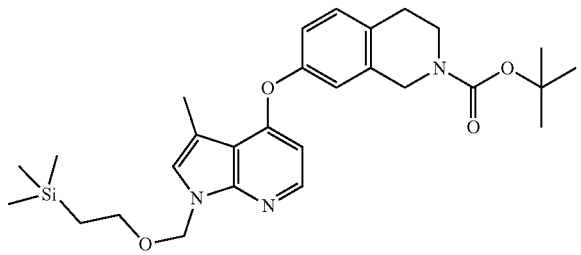 [SMILES: Cc1cn(COCC[Si](C)(C)C)c2nccc(Oc3ccc4c(c3)CN(C(=O)OC(C)(C)C)CC4)c12]

tert-Butyl 7-((3-methyl-1-((2-(trimethylsilyl)ethoxy)methyl)-1H-pyrrolo[2,3-b]pyridin-4-yl)oxy)-3,4-dihydroisoquinoline-2(1H)-carboxylate (Intermediate 1B-a)

A stirred solution of Intermediate 1A-a (1.50 g, 4.39 mmol) in toluene (25 mL) was degassed with argon for 30 min. tert-Butyl 7-hydroxy-3,4-dihydroisoquinoline-2(1H)-carboxylate (1.27 g, 4.84 mmol), potassium carbonate (1.21 g, 8.75 mmol), XPhos (0.22 g, 0.45 mmol)) and $Pd_2(dba)_3$ (0.21 g, 0.23 mmol) were added and the resulting mixture was heated at 100° C. for 18 h. The mixture was allowed to cool to RT and then partitioned between ethyl acetate and water. The organic layer was washed with water and brine, dried ($MgSO_4$) and evaporated. The crude product was chromatographed on a 50 g Si cartridge eluting with 0-25% ethyl acetate in cyclohexane. The product was obtained as a yellow oil (1.45 g).

LCMS (Method 3): Rt=1.99 min, m/z 510.3 $[M+H]^+$

Step C

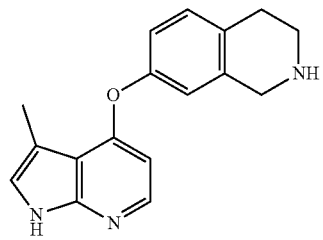 [SMILES: Cc1c[nH]c2nccc(Oc3ccc4c(c3)CNCC4)c12]

7-((3-Methyl-1H-pyrrolo[2,3-b]pyridin-4-yl)oxy)-1,2,3,4-tetrahydroisoquinoline (Example 1)

Intermediate 1B-a (0.20 g, 0.39 mmol) was dissolved in a mixture of DCM (3 mL) and TFA (2 mL) and the reaction was stirred at RT for 2 h. The mixture was diluted with methanol and loaded onto a 5 g SCX-2 cartridge eluting with methanol and then 2M methanolic ammonia. After standing for 18 h, the ammonia solution was evaporated to give a residue which was purified by MDAP (acidic). The resulting gum was freeze dried from a mixture of acetonitrile and water. Trituration using acetonitrile gave example 1 as a white solid (56 mg).

LCMS (Method 1): Rt=3.63 min, m/z 280.2 $[M+H]^+$ $^1$H NMR (400 MHz, $CD_3OD$) δ 8.50 (s, 1H, formic acid), 7.96 (d, J=5.6 Hz, 1H), 7.33 (d, J=8.4 Hz, 1H), 7.09 (dd, J=2.5, 8.4 Hz, 1H), 7.04-7.00 (m, 2H), 6.32 (d, J=5.6 Hz, 1H), 4.31 (s, 2H), 3.48 (dd, J=6.3, 6.3 Hz, 2H), 3.11 (dd, J=6.4, 6.4 Hz, 2H), 2.38 (d, J=1.0 Hz, 3H).

Examples 2 to 26

Preparation of Intermediates 1A-b, 1A-c and 1A-d

The following intermediates were prepared in a similar manner to Intermediate 1A-a from the indicated starting materials.

| Intermediate | Structure | Starting materials | LC-MS |
| --- | --- | --- | --- |
| 1A-b | (structure shown) | 4-Bromo-1H-pyrrolo[2,3-b]pyridine | Rt = 1.94 min, m/z 327.2/329.1 $[M + H]^+$ (Method 3) |

-continued

| Intermediate | Structure | Starting materials | LC-MS |
|---|---|---|---|
| 1A-c | 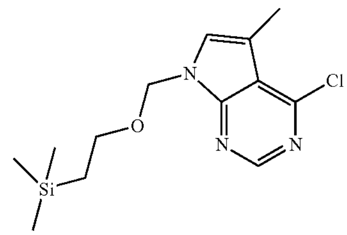 [SMILES: Cc1cn(COCC[Si](C)(C)C)c2ncnc(Cl)c12] | 4-Chloro-5-methyl-7H-pyrrolo[2,3-d]pyrimidine | Rt = 1.73 min, m/z 298.1/300.1 [M + H]+ (Method 3) |
| 1A-d | 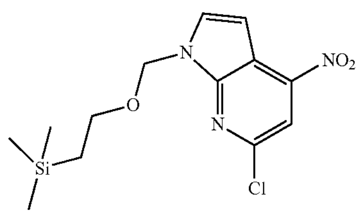 [SMILES: C[Si](C)(C)CCOCn1ccc2c([N+](=O)[O-])cc(Cl)nc21] | 6-Chloro-4-nitro-1H-pyrrolo[2,3-b]pyridine | Rt = 4.71 min, m/z no mass ion observed (Method 6) $^1$H NMR (400 MHz, CDCl$_3$) δ 7.99 (s, 1H), 7.68 (d, J = 3.8 Hz, 1H), 7.24 (d, J = 3.8 Hz, 1H), 5.75 (s, 2H), 3.60 (m, 2H), 0.98 (m, 2H), 0.00 (s, 9H). |

Intermediate 13

Di-tert-butyl 2-(4-hydroxyphenyl)piperazine-1,4-dicarboxylate (Intermediate 13)

tert-Butyl 3-(4-hydroxyphenyl)piperazine-1-carboxylate (300 mg, 1.08 mmol) and DIPEA (281 μL, 1.62 mmol) were dissolved in DCM (5 mL) and the solution was cooled in an ice bath. Di-tert-butyl dicarbonate (259 mg, 1.19 mmol) was added and the reaction was stirred whilst being allowed to warm to RT. After stirring for 18 h the reaction mixture was diluted with DCM and the solution was washed with water and brine, dried (Na$_2$SO$_4$) and evaporated. The product was used without further purification.

LCMS (Method 5): Rt=3.11 min, m/z 379.2 [M+H]+

The following examples were prepared in a similar way to Example 1 by combining in step B either intermediate 1A-a, 1A-b or 1A-c and a suitable phenol, including Intermediate 13, as indicated in the following table 2.

TABLE 2

| Ex. | Structure | Intermediates in step 2 | 1H NMR | LC-MS |
|---|---|---|---|---|
| 2 | 4-(isoindolin-5-yloxy)-3-methyl-1H-pyrrolo[2,3-b]pyridine | Intermediate 1A-a and tert-butyl 5-hydroxyisoindoline-2-carboxylate | $^1$H NMR (400 MHz, d6-DMSO) δ 11.34 (s, 1H), 7.99 (d, J = 5.4 Hz, 1H), 7.31 (d, J = 8.1 Hz, 1H), 7.11 (s, 1H), 7.04 (d, J = 2.1 Hz, 1H), 6.96 (dd, J = 2.2, 8.0 Hz, 1H), 6.24 (d, J = 5.4 Hz, 1H), 4.06 (s, 4H), 2.34 (d, J = 0.9 Hz, 3H). | Rt = 1.76 min, m/z 266.0 [M + H]+ (Method 1) |

TABLE 2-continued

| Ex. | Structure | Intermediates in step 2 | 1H NMR | LC-MS |
|---|---|---|---|---|
| 3 | N-methyl-1-(4-((3-methyl-1H-pyrrolo[2,3-b]pyridin-4-yl)oxy)phenyl)methanamine | Intermediate 1A-a and tert-butyl (4-hydroxybenzyl)(methyl)carbamate | $^1$H NMR (400 MHz, d6-DMSO) δ 11.34 (s, 1H), 8.00 (d, J = 5.4 Hz, 1H), 7.38 (d, J = 8.7 Hz, 2H), 7.13-7.10 (m, 1H), 7.08 (d, J = 8.5 Hz, 2H), 6.25 (d, J = 5.4 Hz, 1H), 3.65 (s, 2H), 2.32 (d, J = 1.1 Hz, 3H), 2.27 (s, 3H). | Rt = 1.83 min, m/z 268.1 [M + H]$^+$ (Method 1) |
| 4 | 2-(4-((1H-pyrrolo[2,3-b]pyridin-4-yl)oxy)phenyl)ethanamine | Intermediate 1A-b and tert-butyl (4-hydroxyphenethyl)carbamate | $^1$H NMR (400 MHz, d6-DMSO) δ 11.71 (s, 1H), 8.07 (d, J = 5.4 Hz, 1H), 7.34 (d, J = 3.4 Hz, 1H), 7.28 (d, J = 8.5 Hz, 2H), 7.10 (d, J = 8.5 Hz, 2H), 6.39 (d, J = 5.4 Hz, 1H), 6.19 (d, J = 3.4 Hz, 1H), 2.79 (dd, J = 7.0, 7.0 Hz, 2H), 2.67 (dd, J = 7.1, 7.1 Hz, 2H) | Rt = 1.68 min, m/z 254.4 [M + H]$^+$ (Method 1) |
| 5 | 7-((3-methyl-1H-pyrrolo[2,3-b]pyridin-4-yl)oxy)-2,3,4,5-tetrahydro-1H-benzo[d]azepine | Intermediate 1A-a and tert-butyl 7-hydroxy-1,2,4,5-tetrahydro-3H-benzo[d]azepine-3-carboxylate | $^1$H NMR (400 MHz, d6-DMSO) δ 11.33 (s, 1H), 7.99 (d, J = 5.4 Hz, 1H), 7.15 (d, J = 8.1 Hz, 1H), 7.12-7.08 (m, 1H), 6.92 (d, J = 2.6 Hz, 1H), 6.83 (dd, J = 2.6, 8.1 Hz, 1H), 6.24 (d, J = 5.4 Hz, 1H), 2.88-2.73 (m, 8H), 2.34 (d, J = 1.0 Hz, 3H). | Rt = 1.99 min, m/z 293.9 [M + H]$^+$ (Method 1) |
| 6 | 7-((5-methyl-7H-pyrrolo[2,3-d]pyrimidin-4-yl)oxy)-1,2,3,4-tetrahydroisoquinoline | Intermediate 1A-c and tert-butyl 7-hydroxy-3,4-dihydroisoquinoline-2(1H)-carboxylate | $^1$H NMR (400 MHz, CDCl$_3$) δ 9.08 (s, 1H), 8.37 (s, 1H), 7.17 (d, J = 8.2 Hz, 1H), 7.02 (dd, J = 2.5, 8.3 Hz, 1H), 6.95 (s, 1H), 6.91 (d, J = 2.3 Hz, 1H), 4.05 (s, 2H), 3.16 (t, J = 6.0 Hz, 2H), 2.81 (t, J = 5.9 Hz, 2H), 2.49 (d, J = 1.2 Hz, 3H). | Rt = 2.35 min, m/z 281.4 [M + H]$^+$ (Method 2) |

TABLE 2-continued

| Ex. | Structure | Intermediates in step 2 | 1H NMR | LC-MS |
|---|---|---|---|---|
| 7 | 5-methyl-4-(4-(pyrrolidin-3-yl)phenoxy)-7H-pyrrolo[2,3-d]pyrimidine | Intermediate 1A-c and tert-butyl 3-(4-hydroxyphenyl)pyrrolidine-1-carboxylate | $^1$H NMR (400 MHz, CDCl$_3$ + a drop of CD$_3$OD) δ 8.27 (s, 1H), 7.32 (d, J = 8.5 Hz, 2H), 7.19 (d, J = 8.5 Hz, 2H), 6.98 (s, 1H), 3.41-3.34 (m, 1H), 3.35-3.26 (m, 1H), 3.22-3.14 (m, 1H), 3.14-3.04 (m, 1H), 2.87 (dd, J = 8.5, 10.6 Hz, 1H), 2.49 (s, 3H), 2.35-2.25 (m, 1H), 1.99-1.85 (m, 1H). | Rt = 2.48 min, m/z 295.4 [M + H]$^+$ (Method 2) |
| 8 | 2-(4-((5-methyl-7H-pyrrolo[2,3-d]pyrimidin-4-yl)oxy)phenyl)ethanamine | Intermediate 1A-c and tert-butyl (4-hydroxyphenethyl)carbamate | $^1$H NMR (400 MHz, CDCl$_3$) δ 9.04 (s, 1H), 8.30 (s, 1H), 7.22 (d, J = 8.6 Hz, 2H), 7.13 (d, J = 8.5 Hz, 2H), 6.91-6.87 (m, 1H), 2.94 (t, J = 6.9 Hz, 2H), 2.72 (t, J = 6.9 Hz, 2H), 2.43 (d, J = 1.2 Hz, 3H), 1.19 (s, 2H). | Rt = 2.43 min, m/z 269.3 [M + H]$^+$ (Method 2) |
| 9 | (4-((5-methyl-7H-pyrrolo[2,3-d]pyrimidin-4-yl)oxy)phenyl)methanamine | Intermediate 1A-c and tert-butyl (4-hydroxybenzyl)carbamate | $^1$H NMR (400 MHz, CD$_3$OD) δ 8.15 (s, 1H), 7.44 (d, J = 8.5 Hz, 2H), 7.20 (d, J = 8.4 Hz, 2H), 7.08 (d, J = 1.0 Hz, 1H), 3.87 (s, 2H), 2.47 (d, J = 1.0 Hz, 3H). | Rt = 2.25 min, m/z 255.3 [M + H]$^+$ (Method 2) |
| 10 | 2-methyl-7-((3-methyl-1H-pyrrolo[2,3-b]pyridin-4-yl)oxy)-1,2,3,4-tetrahydroisoquinoline | Intermediate 1A-a and 2-methyl-1,2,3,4-tetrahydroisoquinolin-7-ol | $^1$H NMR (400 MHz, d6-DMSO) δ 11.35 (s, 1H), 7.98 (d, J = 5.4 Hz, 1H), 7.17 (d, J = 8.2 Hz, 1H), 7.11 (s, 1H), 6.94-6.85 (m, 2H), 6.23 (d, J = 5.4 Hz, 1H), 3.46 (s, 2H), 2.82 (t, J = 5.3 Hz, 2H), 2.60 (t, J = 5.6 Hz, 2H), 2.33 (d, J = 4.0 Hz, 6H). | Rt = 1.91 min, m/z 294.4 [M + H]$^+$ (Method 2) |

TABLE 2-continued

| Ex. | Structure | Intermediates in step 2 | 1H NMR | LC-MS |
|---|---|---|---|---|
| 11 | 6-((3-methyl-1H-pyrrolo[2,3-b]pyridin-4-yl)oxy)-1,2,3,4-tetrahydroisoquinoline | Intermediate 1A-a and tert-butyl 6-hydroxy-3,4-dihydroisoquinoline-2(1H)-carboxylate | $^1$H NMR (400 MHz, d6-DMSO) δ 11.32 (s, 1H), 7.99 (d, J = 5.4 Hz, 1H), 7.11-7.07 (m, 2H), 6.91-6.86 (m, 2H), 6.23 (d, J = 5.4 Hz, 1H), 3.84 (s, 2H), 2.93 (t, J = 5.8 Hz, 2H), 2.68 (t, J = 5.6 Hz, 2H), 2.34 (d, J = 0.8 Hz, 3H). | Rt = 1.85 min, m/z 280.3 [M + H]$^+$ (Method 1) |
| 12 | (3-fluoro-4-((3-methyl-1H-pyrrolo[2,3-b]pyridin-4-yl)oxy)phenyl)methanamine | Intermediate 1A-a and tert-butyl (3-fluoro-4-hydroxybenzyl)carbamate | $^1$H NMR (400 MHz, d6-DMSO) δ 11.42-11.36 (m, 1H), 7.98 (d, J = 5.4 Hz, 1H), 7.42 (dd, J = 1.6, 12.0 Hz, 1H), 7.29-7.20 (m, 2H), 7.14 (s, 1H), 6.14 (dd, J = 0.9, 5.4 Hz, 1H), 3.75 (s, 2H), 2.39 (d, J = 1.0 Hz, 3H), 1.97 (s, 2H). | Rt = 1.88 min, m/z 272.2 [M + H]$^+$ (Method 1) |
| 13 | 3-methyl-4-(4-(piperazin-2-yl)phenoxy)-1H-pyrrolo[2,3-b]pyridine | Intermediate 1A-a and Intermediate 13 | $^1$H NMR (400 MHz, d6-DMSO) δ 11.36 (s, 1H), 8.00 (d, J = 5.4 Hz, 1H), 7.48-7.41 (m, 2H), 7.13-7.10 (m, 1H), 7.10-7.05 (m, 2H), 6.27-6.24 (m, 1H), 3.78-3.57 (m, 1H), 2.98-2.54 (m, 6H), 2.31-2.30 (m, 4H), 2.07-1.81 (m, 1H). | Rt = 2.95 min, m/z 309.3 [M + H]$^+$ (Method 1) |
| 14 | 5-((3-methyl-1H-pyrrolo[2,3-b]pyridin-4-yl)oxy)-2,3-dihydro-1H-inden-2-amine | Intermediate 1A-a and tert-butyl (5-hydroxy-2,3-dihydro-1H-inden-2-yl)carbamate | $^1$H NMR (400 MHz, DMSO) δ 11.33 (s, 1H), 7.98 (d, J = 5.4 Hz, 1H), 7.23 (d, J = 8.1 Hz, 1H), 7.10 (s, 1H), 6.97 (d, J = 2.1 Hz, 1H), 6.89 (dd, J = 2.4, 8.0 Hz, 1H), 6.22 (d, J = 5.4 Hz, 1H), 3.76-3.68 (m, 1H), 3.03 (dd, J = 6.8, 15.7 Hz, 2H), 2.61-2.53 (m, 2H), 2.34 (d, J = 1.0 Hz, 3H), 2.03 (s, 2H). | Rt = 1.93 min, m/z 280.2 [M + H]$^+$ (Method 1) |

TABLE 2-continued

| Ex. | Structure | Intermediates in step 2 | 1H NMR | LC-MS |
|---|---|---|---|---|
| 15 | 7-((3-methyl-1H-pyrrolo[2,3-b]pyridin-4-yl)oxy)-2,3,4,5-tetrahydro-1H-benzo[c]azepine | Intermediate 1A-a and tert-butyl 7-hydroxy-1,3,4,5-tetrahydro-2H-benzo[c]azepine-2-carboxylate | $^1$H NMR (400 MHz, d6-DMSO) δ 11.34 (s, 1H), 7.99 (d, J = 5.4 Hz, 1H), 7.16 (d, J = 8.2 Hz, 1H), 7.11 (s, 1H), 6.97 (d, J = 2.5 Hz, 1H), 6.83 (dd, J = 2.6, 8.0 Hz, 1H), 6.24 (d, J = 5.4 Hz, 1H), 3.79 (s, 2H), 3.06-3.00 (m, 2H), 2.89-2.84 (m, 2H), 2.33 (d, J = 1.0 Hz, 3H), 1.64-1.57 (m, 2H). | Rt = 1.94 min, m/z 294.3 [M + H]$^+$ (Method 1) |
| 16 | 8-((3-methyl-1H-pyrrolo[2,3-b]pyridin-4-yl)oxy)-2,3,4,5-tetrahydro-1H-benzo[c]azepine | Intermediate 1A-a and tert-butyl 8-hydroxy-1,3,4,5-tetrahydro-2H-benzo[c]azepine-2-carboxylate | $^1$H NMR (400 MHz, d6-DMSO) δ 11.34 (s, 1H), 8.29 (s, 1H), 8.00 (d, J = 5.4 Hz, 1H), 7.24 (d, J = 8.1 Hz, 1H), 7.12 (s, 1H), 7.03-7.01 (m, 1H), 6.93 (dd, J = 2.6, 8.1 Hz, 1H), 6.25 (d, J = 5.4 Hz, 1H), 3.90 (s, 2H), 3.16-3.09 (m, 2H), 2.95-2.89 (m, 2H), 2.34 (d, J = 0.8 Hz, 3H), 1.72-1.64 (m, 2H). | Rt = 2.03 min, m/z 294.2 [M + H]$^+$ (Method 1) |
| 17 | 4-(4-(azetidin-3-yl)phenoxy)-3-methyl-1H-pyrrolo[2,3-b]pyridine | Intermediate 1A-a and tert-butyl 3-(4-hydroxyphenyl)azetidine-1-carboxylate | $^1$H NMR (400 MHz, d6-DMSO) δ 11.38 (s, 1H), 8.02 (d, J = 5.4 Hz, 1H), 7.48 (d, J = 8.6 Hz, 2H), 7.18-7.13 (m, 3H), 6.28 (d, J = 5.4 Hz, 1H), 4.23-4.08 (m, 3H), 4.04-3.98 (m, 2H), 2.31 (d, J = 0.9 Hz, 3H). | Rt = 1.88 min, m/z 280.3 [M + H]$^+$ (Method 1) |
| 18 | 3-methyl-4-(4-(pyrrolidin-2-yl)phenoxy)-1H-pyrrolo[2,3-b]pyridine | Intermediate 1A-a and tert-butyl 2-(4-hydroxyphenyl)pyrrolidine-1-carboxylate | $^1$H-NMR (400 MHz, d6-DMSO) δ 11.32 (br s, 1H), 7.98 (d, J = 5.5 Hz, 1H), 7.41 (d, J = 8.4 Hz, 2H), 7.09 (s, 1H), 7.05 (d, J = 8.4 Hz, 2H), 6.23 (d, J = 5.5 Hz, 1H), 4.03 (t, J = 7.6 Hz, 1H), 3.04-2.96 (m, 1H), 2.91-2.82 (m, 1H), 2.31 (s, 3H), 2.15-2.05 (m, 1H), 1.84-1.66 (m, 2H), 1.52-1.40 (m, 1H). | Rt = 0.37 min, m/z 294.2 [M − H]$^+$ (Method 7) |

TABLE 2-continued

| Ex. | Structure | Intermediates in step 2 | 1H NMR | LC-MS |
|---|---|---|---|---|
| 19 | 2-(4-((3-methyl-1H-pyrrolo[2,3-b]pyridin-4-yl)oxy)phenyl)ethanamine | Intermediate 1A-a and tert-butyl (4-hydroxy-phenethyl)carbamate | ¹H-NMR (400 MHz, d6-DMSO) δ 11.35 (bs, 1H), 8.35 (s, 1H), 7.99 (d, J = 5.3 Hz, 1H), 7.30 (d, J = 8.4 Hz, 2H), 7.10 (s, 1H), 7.08 (d, J = 8.4 Hz, 2H), 6.24 (d, J = 5.3 Hz, 1H), 3.00-2.92 (m, 2H), 2.84-2.76 (m, 2H), 2.52 (s, 2H), 2.30 (d, J = 0.9 Hz, 3H). | Rt = 0.41 min, m/z 268.2 [M − H]⁺ (Method 7) |
| 20 | 3-methyl-4-(4-(pyrrolidin-3-yl)phenoxy)-1H-pyrrolo[2,3-b]pyridine | Intermediate 1A-a and tert-butyl 3-(4-hydroxyphenyl)pyrrolidine-1-carboxylate | ¹H-NMR (400 MHz, d6-DMSO) δ 11.34 (bs, 1H), 7.99 (d, J = 5.5 Hz, 1H), 7.33 (d, J = 8.6 Hz, 2H), 7.11 (s, 1H), 7.06 (d, J = 8.6 Hz, 2H), 6.24 (d, J = 5.5 Hz, 1H), 3.24-3.08 (m, 2H), 3.01-2.84 (m, 2H), 2.62 (dd, J = 9.8, 7.6 Hz, 1H), 2.32 (d, J = 0.7 Hz, 3H), 2.18-2.09 (m, 1H), 1.72-1.62 (m, 1H). | Rt = 0.40 min, m/z 294.3 [M − H]⁺ (Method 7) |
| 21 | (4-((3-methyl-1H-pyrrolo[2,3-b]pyridin-4-yl)oxy)phenyl)methanamine | Intermediate 1A-a and tert-butyl (4-hydroxybenzyl)carbamate | ¹H-NMR (400 MHz, d6-DMSO) δ 11.34 (bs, 1H), 7.99 (d, J = 5.5 Hz, 1H), 7.39 (d, J = 8.5 Hz, 2H), 7.11 (bs, 1H), 7.07 (d, J = 8.5 Hz, 2H), 6.23 (d, J = 5.5 Hz, 1H), 3.72 (s, 2H), 2.33 (d, J = 0.7 Hz, 3H). | Rt = 0.29 min, m/z 254.2 [M − H]⁺ (Method 7) |
| 22 | 3-methyl-4-(4-(2-(pyrrolidin-1-yl)ethyl)phenoxy)-1H-pyrrolo[2,3-b]pyridine | Intermediate 1A-a and 4-(2-(pyrrolidin-1-yl)ethyl)phenol | ¹H-NMR (400 MHz, d6-DMSO) δ 11.34 (s, 1H), 8.18 (s, 2H), 8.05 and 7.98 (d, J = 5.4 Hz, 1H), 7.30 (d, J = 8.6 Hz, 2H), 7.22 and 7.10 (d, J = 0.8 Hz, 1H), 7.05 (d, J = 8.6 Hz, 2H), 6.29 and 6.22 (d, J = 5.4 Hz, 1H), 2.78 (m, 4H), 2.64 (m, 4H), 2.31 and 2.30 (d, J = 0.8 Hz, 3H), 1.74 -1.69 (m, 4H). | Rt = 0.38 min, m/z 322.3 [M − H]⁺ (Method 7) |

TABLE 2-continued

| Ex. | Structure | Intermediates in step 2 | 1H NMR | LC-MS |
|---|---|---|---|---|
| 23 | 1-(3-fluoro-4-((3-methyl-1H-pyrrolo[2,3-b]pyridin-4-yl)oxy)phenyl)ethanamine | Intermediate 1A-a and tert-butyl (1-(3-fluoro-4-hydroxyphenyl)ethyl)carbamate | $^1$H-NMR (400 MHz, d6-DMSO) δ 11.39 (bs, 1H), 8.24 (s, 1H), 7.99 (d, J = 5.5 Hz, 1H), 7.53-7.48 (m, 1H), 7.31-7.27 (m, 2H), 7.13 (s, 1H), 6.15 (d, J = 5.5 Hz, 1H), 4.20 (q, J = 6.7 Hz, 1H), 2.35 (d, J = 0.9 Hz, 3H), 1.36 (d, J = 6.7 Hz, 3H). | Rt = 0.33 min, m/z 286.2 [M − H]$^+$ (Method 7) |
| 24 | 1-(4-((3-methyl-1H-pyrrolo[2,3-b]pyridin-4-yl)oxy)phenyl)ethanamine | Intermediate 1A-a and tert-butyl (1-(4-hydroxyphenyl)ethyl)carbamate | $^1$H-NMR (400 MHz, d6-DMSO) δ 11.32 (bs, 1H), 7.98 (d, J = 5.5 Hz, 1H), 7.42 (d, J = 8.6 Hz, 2H), 7.09 (s, 1H), 7.05 (d, J = 8.6 Hz, 2H), 6.22 (d, J = 5.5 Hz, 1H), 4.54 (m, 2H), 4.00 (q, J = 6.6 Hz, 1H), 2.32-2.30 (d, J = 0.9 Hz, 3H), 1.24 (d, J = 6.6 Hz, 3H). | Rt = 0.17 min, m/z 268.1 [M − H]$^+$ (Method 7) |
| 25 | 2-(4-((3-methyl-1H-pyrrolo[2,3-b]pyridin-4-yl)oxy)phenyl)propan-2-amine | Intermediate 1A-a and tert-butyl (2-(4-hydroxyphenyl)propan-2-yl)carbamate | $^1$H-NMR (400 MHz, d6-DMSO) δ 11.36 (bs, 1H), 8.29 (s, 1H), 8.00 (d, J = 5.3 Hz, 1H), 7.58 (d, J = 8.8 Hz, 2H), 7.14-7.06 (m, 3H), 6.26 (d, J = 5.5 Hz, 1H), 2.30 (d, J = 0.9 Hz, 3H), 1.48 (s, 6H). | Rt = 0.37 min, m/z 282.2 [M − H]$^+$ (Method 7) |
| 26 | 6-((3-methyl-1H-pyrrolo[2,3-b]pyridin-4-yl)oxy)-1,2,3,4-tetrahydronaphthalen-1-amine | Intermediate 1A-a and tert-butyl (6-hydroxy-1,2,3,4-tetrahydronaphthalen-1-yl)carbamate | $^1$H-NMR (400 MHz, d6-DMSO) δ 11.35 (s, 1H), 8.30 (s, 1H), 8.00 (d, J = 5.5 Hz, 1H), 7.52 (d, J = 8.5 Hz, 1H), 7.10 (s, 1H), 6.95 (dd, J = 8.5, 2.2 Hz, 1H), 6.86 (d, J = 2.2 Hz, 1H), 6.26 (d, J = 5.5 Hz, 1H), 4.12-4.05 (m, 1H), 2.78-2.61 (m, 2H), 2.30 (s, 3H), 2.01-1.82 (m, 2H), 1.76-1.61 (m, 2H). | Rt = 0.42 min, m/z 294.2 [M − H]$^+$ (Method 7) |

Example 27

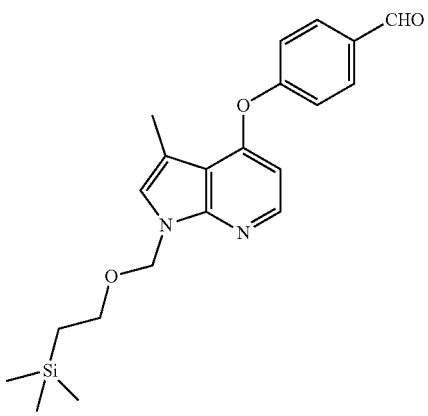 [SMILES: Cc1cn(COCC[Si](C)(C)C)c2nccc(Oc3ccc(C=O)cc3)c12]

4-((3-Methyl-1-((2-(trimethylsilyl)ethoxy)methyl)-1H-pyrrolo[2,3-b]pyridin-4-yl)oxy)benzaldehyde (Intermediate 27A)

Intermediate 1A-a (460 mg, 1.35 mmol) was dissolved in toluene (10 mL) and the solution was bubbled with argon for 20 min. 4-Hydroxybenzaldehyde (185 mg, 1.48 mmol), Pd$_2$(dba)$_3$ (64 mg, 0.068 mmol), XPhos (66 mg, 0.14 mmol) and potassium carbonate (374 mg, 2.70 mmol) were added and the reaction was stirred under argon at 100° C. After 18 h, the reaction mixture was allowed to cool and partitioned between ethyl acetate and water. The organic layer was washed with brine, dried (MgSO$_4$) and evaporated. The crude product was purified on a 25 g Si cartridge eluting with 0-25% ethyl acetate in cyclohexane to give the title compound (240 mg).

LCMS (Method 3): Rt=1.79 min, m/z 383.2 [M+H]$^+$

Step B

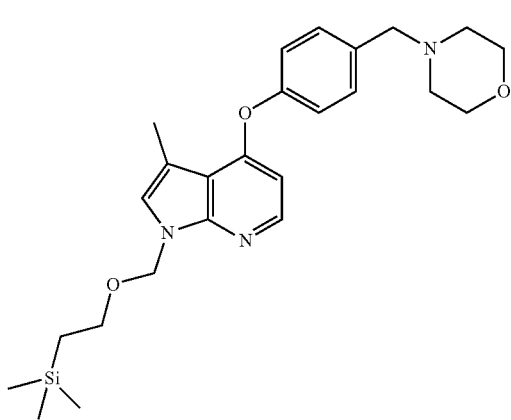 [SMILES: Cc1cn(COCC[Si](C)(C)C)c2nccc(Oc3ccc(CN4CCOCC4)cc3)c12]

4-(4-((3-Methyl-1-((2-(trimethylsilyl)ethoxy)methyl)-1H-pyrrolo[2,3-b]pyridin-4-yl)oxy)benzyl)morpholine (Intermediate 27B)

A solution of intermediate 27A (120 mg, 0.31 mmol) and morpholine (27 μL, 0.31 mmol) in DCE (10 mL) containing some 4 Å molecular sieves was treated with sodium triacetoxyborohydride (133 mg, 0.60 mmol). The reaction was stirred at RT overnight and then a further quantity of sodium triacetoxyborohydride (180 mg, 0.85 mmol) was added. Stirring was continued for a further 4 h before another quantity of sodium triacetoxyborohydride (170 mg, 0.80 mmol) was added. After another 4 h, the mixture was partitioned between DCM and water. The organic layer was washed with water and brine, dried (Na$_2$SO$_4$) and evaporated. The crude product was used without further purification.

LCMS (Method 3): Rt=1.18 min, m/z 454.3 [M+H]$^+$

Step C

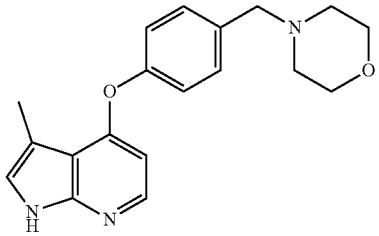 [SMILES: Cc1c[nH]c2nccc(Oc3ccc(CN4CCOCC4)cc3)c12]

4-(4-((3-Methyl-1H-pyrrolo[2,3-b]pyridin-4-yl)oxy)benzyl)morpholine

Example 27

Example 27 was prepared from intermediate 27B using a method analogous to that used in the preparation of example 1, step C.

LCMS (Method 1): Rt=1.89 min, m/z 324.0 [M+H]$^+$ $^1$H NMR (400 MHz, d6-DMSO) δ 11.35 (s, 1H), 8.01 (d, J=5.4 Hz, 1H), 7.37 (d, J=8.6 Hz, 2H), 7.14-7.11 (m, 1H), 7.09 (d, J=8.7 Hz, 2H), 6.28 (d, J=5.4 Hz, 1H), 3.60-3.56 (m, 4H), 3.47 (s, 2H), 2.39-2.33 (m, 4H), 2.30 (d, J=1.0 Hz, 3H).

The following examples were prepared as described for the preparation of Example 27 Step B and C, replacing the morpholine used in Step B with the proper amine indicated in the following table 3.

TABLE 3

| Ex. | Structure | Amine used in Step B | 1H NMR | LC-MS |
|---|---|---|---|---|
| 28 | 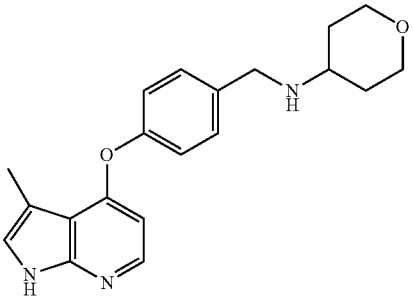<br>N-(4-((3-methyl-1H-pyrrolo[2,3-b]pyridin-4-yl)oxy)benzyl)tetrahydro-2H-pyran-4-amine | Tetrahydro-2H-pyran-4-amine | $^1$H NMR (400 MHz, d6-DMSO) δ 11.34 (s, 1H), 8.00 (d, J = 5.4 Hz, 1H), 7.41 (d, J = 8.6 Hz, 2H), 7.13-7.10 (m, 1H), 7.08 (d, J = 8.6 Hz, 2H), 6.25 (d, J = 5.4 Hz, 1H), 3.86-3.79 (m, 2H), 3.74 (s, 2H), 3.29-3.22 (m, 2H), 2.64-2.57 (m, 1H), 2.32 (d, J = 1.0 Hz, 3H), 2.05 (s, 1H), 1.82-1.74 (m, 2H), 1.34-1.22 (m, 2H). | Rt = 1.96 min, m/z 338.1 [M + H]$^+$ (Method 1) |
| 29 | 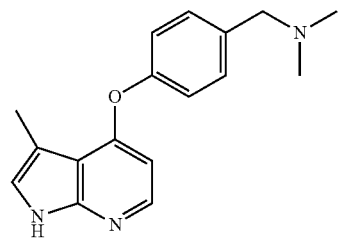<br>N,N-dimethyl-1-(4-((3-methyl-1H-pyrrolo[2,3-b]pyridin-4-yl)oxy)benzyl)methanamine | Dimethylamine | $^1$H NMR (400 MHz, d6-DMSO) δ 11.38 (s, 1H), 8.01 (d, J = 5.4 Hz, 1H), 7.35 (d, J = 8.6 Hz, 2H), 7.14-7.11 (m, 1H), 7.09 (d, J = 8.5 Hz, 2H), 6.28 (d, J = 5.4 Hz, 1H), 3.39 (s, 2H), 2.30 (d, J = 1.0 Hz, 3H), 2.15 (s, 6H). | Rt = 1.88 min, m/z 282.4 [M + H]$^+$ (Method 2) |
| 30 | 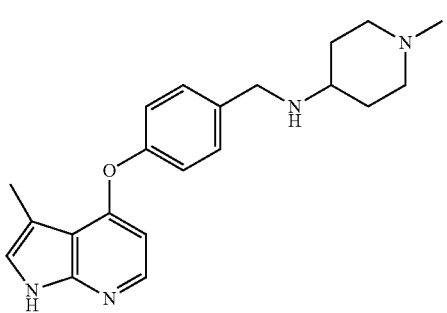<br>1-methyl-N-(4-((3-methyl-1H-pyrrolo[2,3-b]pyridin-4-yl)oxy)benzyl)piperidin-4-amine | 1-Methylpiperidin-4-amine | $^1$H NMR (400 MHz, d6-DMSO) δ 11.35 (s, 1H), 8.00 (d, J = 5.4 Hz, 1H), 7.40 (d, J = 8.6 Hz, 2H), 7.13-7.10 (m, 1H), 7.07 (d, J = 8.5 Hz, 2H), 6.24 (d, J = 5.4 Hz, 1H), 3.72 (s, 2H), 2.73-2.64 (m, 2H), 2.39-2.33 (m, 1H), 2.32 (d, J = 1.1 Hz, 3H), 2.12 (s, 3H), 2.04-1.91 (m, 1H), 1.88-1.74 (m, 4H), 1.34-1.22 (m, 2H). | Rt = 3.69 min, m/z 351.0 [M + H]$^+$ (Method 1) |

TABLE 3-continued

| Ex. | Structure | Amine used in Step B | 1H NMR | LC-MS |
|---|---|---|---|---|
| 31 | 2-((4-((3-methyl-1H-pyrrolo[2,3-b]pyridin-4-yl)oxy)benzyl)amino)ethanol | 2-Aminoethan-1-ol | $^1$H NMR (400 MHz, MeOD) δ 7.94 (d, J = 5.6 Hz, 1H), 7.44 (d, J = 8.5 Hz, 2H), 7.12 (d, J = 8.6 Hz, 2H), 7.04-7.00 (m, 1H), 6.30 (d, J = 5.6 Hz, 1H), 3.82 (s, 2H), 3.69 (t, J = 5.6 Hz, 2H), 2.75 (t, J = 5.6 Hz, 2H), 2.40 (d, J = 1.0 Hz, 3H). | Rt = 3.42 min, m/z 298.5 [M + H]$^+$ (Method 1) |
| 32 | 4-(4-(2,7-diazaspiro[4.4]nonan-2-ylmethyl)phenoxy)-3-methyl-1H-pyrrolo[2,3-b]pyridine | tert-butyl 2,7-diazaspiro[4.4]nonane-2-carboxylate | $^1$H NMR (400 MHz, MeOD) δ 7.95 (d, J = 5.6 Hz, 1H), 7.43 (d, J = 8.5 Hz, 2H), 7.11 (d, J = 8.4 Hz, 2H), 7.04-7.00 (m, 1H), 6.31 (d, J = 5.6 Hz, 1H), 3.70-3.63 (m, 2H), 3.37-3.31 (m, 1H), 3.03-2.62 (m, 6H), 2.57-2.50 (m, 1H), 2.40 (d, J = 1.0 Hz, 3H), 1.89-1.82 (m, 4H). | Rt = 3.94 min, m/z 363.3 [M + H]$^+$ (Method 1) |
| 33 | 3-methyl-4-(4-((4-methylpiperazin-1-yl)methyl)phenoxy)-1H-pyrrolo[2,3-b]pyridine | 1-Methylpiperazine | $^1$H NMR (400 MHz, MeOD) δ 7.95 (d, J = 5.6 Hz, 1H), 7.42 (d, J = 8.5 Hz, 2H), 7.11 (d, J = 8.5 Hz, 2H), 7.03-7.00 (m, 1H), 6.31 (d, J = 5.6 Hz, 1H), 3.57 (s, 2H), 3.34-3.31 (m, 2H), 2.72-2.42 (m, 6H), 2.40 (d, J = 1.1 Hz, 3H), 2.29 (s, 3H). | Rt = 1.94 min, m/z 337.3 [M + H]$^+$ (Method 1) |

Example 34

Step A

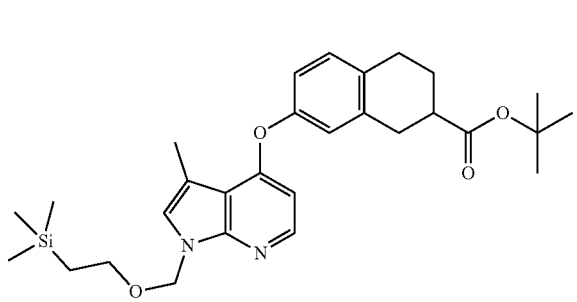 [SMILES: Cc1cn(COCC[Si](C)(C)C)c2nccc(Oc3ccc4c(c3)CC(C(=O)OC(C)(C)C)CC4)c12]

tert-Butyl 7-((3-methyl-1-((2-(trimethylsilyl)ethoxy)methyl)-1H-pyrrolo[2,3-b]pyridin-4-yl)oxy)-3,4-dihydroisoquinoline-2(1H)-carboxylate (Intermediate 34A)

Intermediate 34A was prepared from intermediate 1A-b and tert-butyl 7-hydroxy-3,4-dihydroisoquinoline-2(1H)-carboxylate using an analogous procedure to that used for intermediate 1B-a.

LCMS (Method 3): Rt=1.93 min, m/z 496.3 [M+H]$^+$

Step B

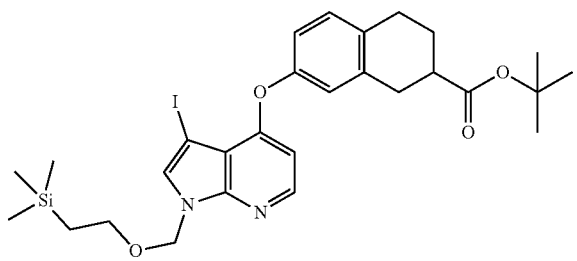 [SMILES: CC(C)(C)OC(=O)C1CCc2ccc(Oc3ccnc4c3c(I)cn4COCC[Si](C)(C)C)cc2C1]

tert-Butyl 7-((3-iodo-1-((2-(trimethylsilyl)ethoxy)methyl)-1H-pyrrolo[2,3-b]-pyridin-4-yl)oxy)-3,4-dihydroisoquinoline-2(1H)-carboxylate (Intermediate 34B)

Intermediate 34A (1.22 g, 2.46 mmol) was dissolved in acetonitrile (25 mL) and the solution was stirred at 0° C. under argon. NIS (600 mg, 2.58 mmol) was added and the reaction was stirred for 30 min at 0° C. Stirring was continued at RT for 1 h and then 1M sodium thiosulfate was added. The product was extracted into ethyl acetate and the combined extracts were washed with water and brine, dried (Na$_2$SO$_4$) and evaporated. The residue was purified by column chromatography on a 25 g Si cartridge eluting with 0-50% ethyl acetate in cyclohexane. The pure product was obtained as a yellow oil (0.87 g).

LCMS (Method 3): Rt=2.02 min, m/z 622.2 [M+H]$^+$

Step C

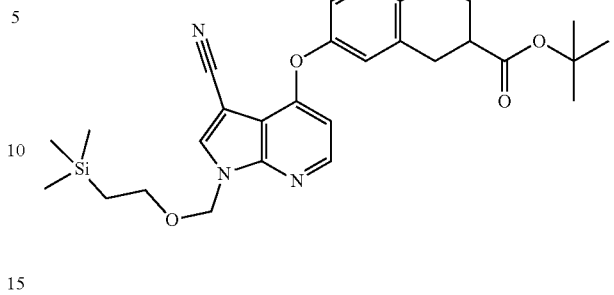

tert-Butyl 7-((3-cyano-1-((2-(trimethylsilyl)ethoxy)methyl)-1H-pyrrolo[2,3-b]pyridin-4-yl)oxy)-3,4-dihydroisoquinoline-2(1H)-carboxylate (Intermediate 34C)

Intermediate 34B (870 mg, 1.40 mmol) was dissolved in DMF (10 mL) and the solution was bubbled with argon for 20 min. Potassium cyanide (228 mg, 3.50 mmol), copper (I) iodide (667 mg, 3.50 mmol), Pd(PPh$_3$)$_4$ (162 mg, 0.14 mmol), and 18-crown-6 (23 mg, 0.084 mmol) were added and the mixture was heated under argon at 110° C. for 2 h. The mixture was allowed to cool and was then partitioned between ethyl acetate and water. The biphasic mixture was filtered and the organic layer was separated, washed with water and brine, dried (Na$_2$SO$_4$) and evaporated. The crude product was purified by chromatography on a 25 g Si cartridge eluting with 0-75% ethyl acetate in cyclohexane. The desired product was obtained as a yellow gum (0.43 g).

LCMS (Method 3): Rt=1.88 min, m/z 521.3 [M+H]$^+$

Step D

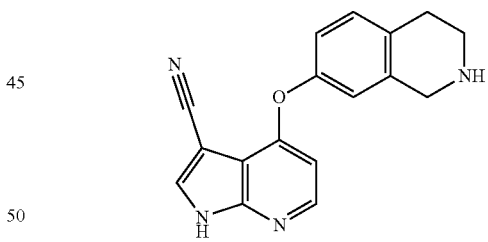

4-((1,2,3,4-Tetrahydroisoquinolin-7-yl)oxy)-1H-pyrrolo[2,3-b]pyridine-3-carbonitrile (Example 34)

Example 34 was prepared from intermediate 34C using a procedure analogous to that used in the preparation of example 1, step C.

LCMS (Method 1): Rt=2.16 min, m/z 291.2 [M+H]$^+$ $^1$H NMR (400 MHz, d6-DMSO) δ 8.39 (s, 1H), 8.27 (s, 1H), 8.20 (d, J=5.6 Hz, 1H), 7.23 (d, J=8.4 Hz, 1H), 7.04 (dd, J=2.4, 8.0 Hz, 1H), 6.99 (d, J=2.3 Hz, 1H), 6.42 (d, J=5.5 Hz, 1H), 3.95-3.91 (m, 3H), 3.03 (t, J=5.9 Hz, 2H), 2.77 (t, J=5.8 Hz, 2H).

Example 35

Step A

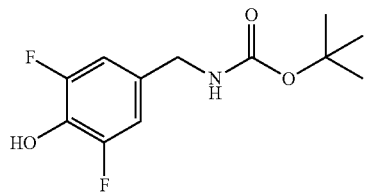 [SMILES: CC(C)(C)OC(=O)NCc1cc(F)c(O)c(F)c1]

tert-Butyl (3,5-difluoro-4-hydroxybenzyl)carbamate (Intermediate 35A)

4-(Aminomethyl)-2,6-difluorophenol (0.5 g, 3.14 mmol) was suspended in a mixture of DCM (10 mL) and THF (5 mL) and DIPEA (1.1 mL, 6.28 mmol) was added. The mixture was cooled in an ice bath and di-tert-butyl dicarbonate (0.76 g, 3.46 mmol) was added. The reaction mixture was allowed to warm to RT and stirred for 16 h. The solvent was evaporated in vacuo and the crude product was chromatographed on a 25 g Si cartridge eluting with 0-100% ethyl acetate in cyclohexane. The product was obtained as a light yellow gum (0.15 g).

LCMS (Method 3): Rt=1.45 min, m/z 260.1 [M+H]$^+$

Step B

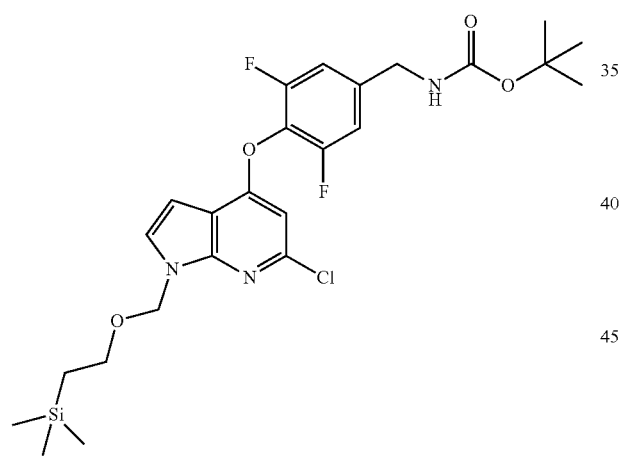

tert-Butyl (4-((6-chloro-1-((2-(trimethylsilyl)ethoxy)methyl)-1H-pyrrolo[2,3-b]-pyridin-4-yl)oxy)-3,5-difluorobenzyl)carbamate (Intermediate 35B)

Intermediate 1A-d (107 mg, 0.326 mmol), Intermediate 35A (129 mg, 0.49 mmol) and potassium carbonate (140 mg, 0.979 mmol) were heated at 120° C. in DMSO (3 mL) for 2 h. The reaction mixture was allowed to cool and then poured into water (10 mL). The product was extracted three times into ethyl acetate and the combined extracts were dried (Na$_2$SO$_4$) and evaporated. The residue was purified by chromatography on a 12 g Si cartridge eluting with 0-40% ethyl acetate in cyclohexane. The product was an off-white solid (240 mg).

LCMS (Method 3): Rt=1.81 min, m/z 540.3 [M+H]$^+$

Step C

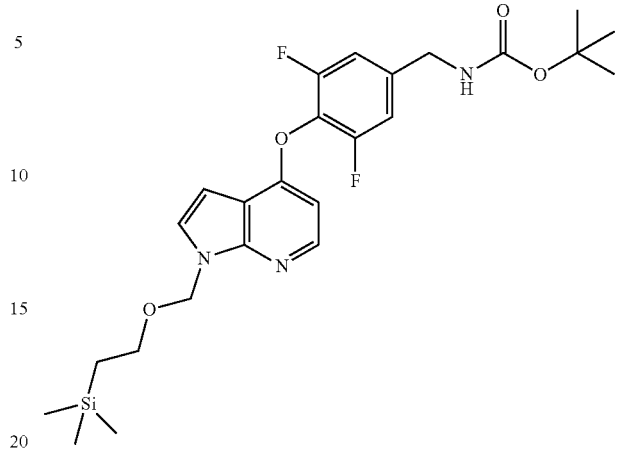

tert-butyl (3,5-difluoro-4-((1-((2-(trimethylsilyl)ethoxy)methyl)-1H-pyrrolo-[2,3-b]pyridin-4-yl)oxy)benzyl)carbamate (Intermediate 35C)

A solution Intermediate 35B (240 mg, 0.45 mmol) and trimethylamine (60 μL, 0.535 mmol) in IMS (20 mL) was stirred over 10% palladium on carbon (24 mg) under a blanket of hydrogen gas. After 18 h at RT, the mixture was filtered through Celite® and the solvent was evaporated to give the title compound as a cream solid (170 mg).

LCMS (Method 3): Rt=1.80 min, m/z 506.3 [M+H]$^+$

Step D

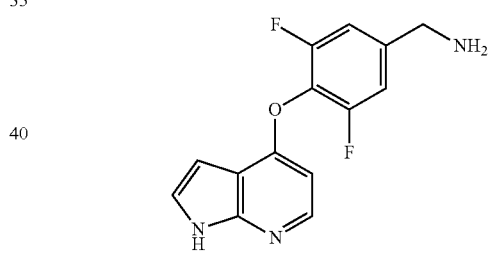

(4-((1H-Pyrrolo[2,3-b]pyridin-4-yl)oxy)-3,5-difluorophenyl)methanamine Example 35

Example 35 was prepared from intermediate 35C using a procedure analogous to that used in the preparation of example 1, step C.

LCMS (Method 1): Rt=1.87 min, m/z 276.2 [M+H]$^+$ $^1$H NMR (400 MHz, MeOD) δ 8.05 (d, J=5.6 Hz, 1H), 7.33-7.30 (m, 3H), 6.42-6.39 (m, 2H), 4.14 (s, 2H).

Example 36

Step A

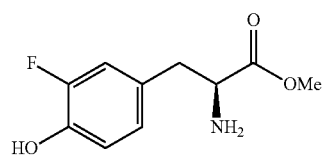 [SMILES: COC(=O)[C@@H](N)Cc1ccc(O)c(F)c1]

Methyl (S)-2-amino-3-(3-fluoro-4-hydroxyphenyl) propanoate (Intermediate 36A)

3-Fluoro-L-tyrosine (6.0 g, 30.12 mmol) was suspended in methanol (120 mL) and the mixture was cooled in an ice bath. Thionyl chloride (11 mL, 150.6 mmol) was added dropwise. The mixture was allowed to warm to RT and then stirred overnight. The solvent was evaporated and the residue dissolved in water (50 mL). After basifying the mixture using saturated aqueous sodium hydrogen carbonate, the product was extracted four times into ethyl acetate. The combined organic extracts were dried ($Na_2SO_4$) and evaporated to give the desired product as a beige solid (4.55 g).

LCMS (Method 3): Rt=0.65 min, m/z 214.1 $[M+H]^+$

Step B

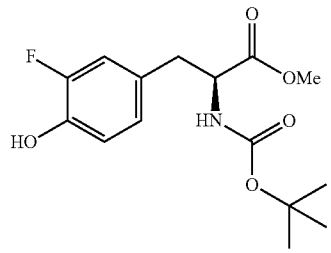 [SMILES: COC(=O)[C@H](Cc1ccc(O)c(F)c1)NC(=O)OC(C)(C)C]

Methyl (S)-2-((tert-butoxycarbonyl)amino)-3-(3-fluoro-4-hydroxyphenyl)-propanoate (Intermediate 36B)

Intermediate 36A (4.55 g, 21.34 mmol) was suspended in a mixture of DCM (153 mL) and THF (77 mL). The mixture was cooled in an ice bath and di-tert-butyl dicarbonate (5.12 g, 23.47 mmol) was added. The reaction mixture was allowed to warm to RT and stirred for 4 h. The solvent was evaporated in vacuo and the crude product was chromatographed on a 120 g Si cartridge eluting with 0-10% 2M methanolic ammonia in DCM. Intermediate 36B was obtained as a yellow gum (5.96 g).

LCMS (Method 3): Rt=1.29 min. m/z 336.2 $[M+Na]^+$

Step C

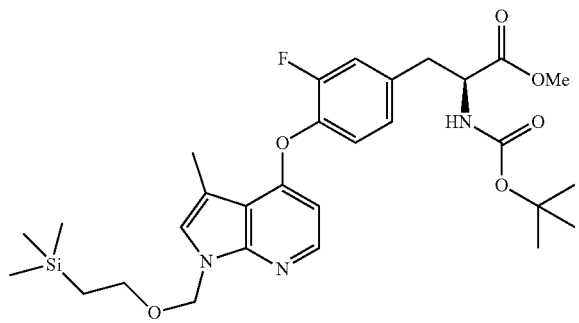 [SMILES: COC(=O)[C@H](Cc1ccc(Oc2ccnc3c2c(C)cn3COCC[Si](C)(C)C)c(F)c1)NC(=O)OC(C)(C)C]

Methyl (S)-2-((tert-butoxycarbonyl)amino)-3-(3-fluoro-4-((3-methyl-1-((2-(trimethylsilyl)ethoxy) methyl)-1H-pyrrolo[2,3-b]pyridin-4-yl)oxy)phenyl)-propanoate (Intermediate 36C)

A mixture of intermediates 1A-a (5.96 g, 19.02 mmol) and 36B (6.09 g, 17.84 mmol), $Pd_2(dba)_3$ (0.82 g, 0.89 mmol), XPhos (0.85 g, 1.78 mmol), and potassium carbonate (5.42 g, 39.25 mmol) in toluene (224 mL) was sonicated for 5 min under a blanket of argon. The mixture was heated at 100° C. for 3 h, and then allowed to cool to RT before filtering through Celite®. The solvent was evaporated and the residue was taken up into water and extracted three times with ethyl acetate. The combined organic extracts were washed with brine, dried ($Na_2SO_4$) and evaporated. The crude product was chromatographed on a 300 g Si cartridge eluting with 0-50% ethyl acetate in cyclohexane. The product was obtained as a beige solid (4.85 g).

LCMS (Method 3): Rt=1.88 min, m/z 574.4 $[M+H]^+$

Step D

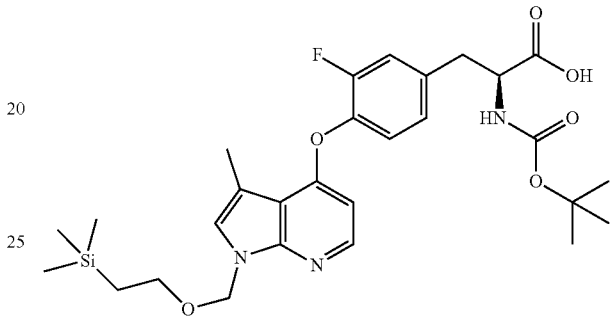

tert-Butyl (S)-(1-(3-fluoro-4-((3-methyl-1-((2-(trimethylsilyl)ethoxy)methyl)-1H-pyrrolo[2,3-b]pyridin-4-yl)oxy)phenyl)-3-hydroxypropan-2-yl)carbamate (Intermediate 36D)

Intermediate 36C (316 mg, 0.55 mmol) was dissolved in THF (10 mL) and sodium borohydride (46 mg, 1.21 mmol) was added. The reaction mixture was stirred at RT overnight. A further portion of sodium borohydride (46 mg, 1.21 mmol) was added and the reaction was stirred at 50° C. for 1 h. After the addition of more sodium borohydride (46 mg, 1.21 mmol) heating was continued for 72 h. After quenching with acetic acid (0.5 mL), water was added and the product was extracted into ethyl acetate. The extract was dried ($Na_2SO_4$) and evaporated. The alcohol was obtained as a colourless oil (463 mg).

LCMS (Method 3): Rt=1.79 min, m/z 546.5 $[M+H]^+$

Step E

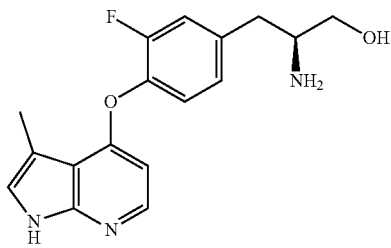 [SMILES: Cc1c[nH]c2nccc(Oc3ccc(C[C@H](N)CO)cc3F)c12]

(S)-2-amino-3-(3-fluoro-4-((3-methyl-1H-pyrrolo[2,3-b]pyridin-4-yl)oxy)phenyl)propan-1-ol (Example 36)

Example 36 was prepared from intermediate 36D using a procedure analogous to that used in the preparation of example 1, step C.

LCMS (Method 1): Rt=1.98 min, m/z 316.3 $[M+H]^+$

¹H NMR (400 MHz, d6-DMSO) δ 11.37 (s, 1H), 7.98 (d, J=5.4 Hz, 1H), 7.29 (dd, J=1.8, 11.8 Hz, 1H), 7.24 (t, J=8.4 Hz, 1H), 7.15-7.09 (m, 2H), 6.17 (d, J=5.4 Hz, 1H), 4.64-4.57 (m, 2H), 3.30-3.17 (m, 1H), 2.92-2.85 (m, 1H), 2.74 (dd, J=5.1, 13.3 Hz, 1H), 2.47-2.43 (m, 1H), 2.38 (d, J=0.9 Hz, 3H), 1.65-1.65 (m, 2H).

The following examples were prepared in a similar manner to example 36 but replacing intermediate 36B with a proper Boc-protected amino ester as starting material in step C.

2-(tert-butyl) 3-methyl (R)-7-hydroxy-3,4-dihydroisoquinoline-2,3(1H)-dicarboxylate (Intermediate 39A)

Intermediate 39A was prepared from methyl(R)-7-hydroxy-1,2,3,4-tetrahydroisoquinoline-3-carboxylate hydrochloride using a similar procedure to that used to prepare intermediate 36B.

LCMS (Method 3): Rt=2.59 min, m/z 306.2 [M−H]⁻

| Ex. | Structure | Boc-protected amino ester | 1H NMR | LC-MS |
|---|---|---|---|---|
| 37 | (S)-2-amino-3-(4-((3-methyl-1H-pyrrolo[2,3-b]pyridin-4-yl)oxy)phenyl)propan-1-ol | Methyl (tert-butoxycarbonyl)-L-tyrosinate | ¹H NMR (400 MHz, d6-DMSO) δ 11.34 (s, 1H), 7.99 (d, J = 5.4 Hz, 1H), 7.28 (d, J = 8.5 Hz, 2H), 7.12-7.10 (m, 1H), 7.06 (d, J = 8.4 Hz, 2H), 6.25 (d, J = 5.4 Hz, 1H), 4.60-4.54 (m, 1H), 3.30-3.25 (m, 1H), 3.23-3.15 (m, 1H), 2.90-2.83 (m, 1H), 2.70 (dd, J = 5.6, 13.3 Hz, 1H), 2.44 (dd, J = 7.8, 13.3 Hz, 1H), 2.33 (d, J = 0.7 Hz, 3H), 1.59 (s, 2H). | Rt = 1.88 min, m/z 298.4 [M + H]⁺ (Method 2) |
| 38 | 2-amino-2-(4-((3-methyl-1H-pyrrolo[2,3-b]pyridin-4-yl)oxy)phenyl)ethanol | Methyl 2-((tert-butoxycarbonyl)-amino)-2-(4-hydroxyphenyl)-acetate | ¹H NMR (400 MHz, d6-DMSO) δ 11.36(s, 1H), 8.00 (d, J = 5.4 Hz, 1H), 7.43 (d, J = 8.6 Hz, 2H), 7.13-7.10 (m, 1H), 7.08 (d, J = 8.6 Hz, 2H), 6.24 (d, J = 5.4 Hz, 1H), 4.77 (t, J = 5.3 Hz, 1H), 3.89 (dd, J = 4.8, 7.8 Hz, 1H), 3.49-3.42 (m, 1H), 3.29-3.25 (m, 1H), 2.33 (d, J = 0.9 Hz, 3H), 1.99 (s, 2H). | Rt = 1.70 min, m/z 284.2 [M + H]⁺ (Method 1) |

Example 39

Step A

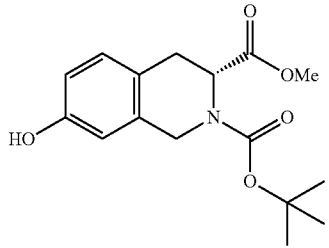 [SMILES: COC(=O)[C@H]1Cc2ccc(O)cc2CN1C(=O)OC(C)(C)C]

Step B

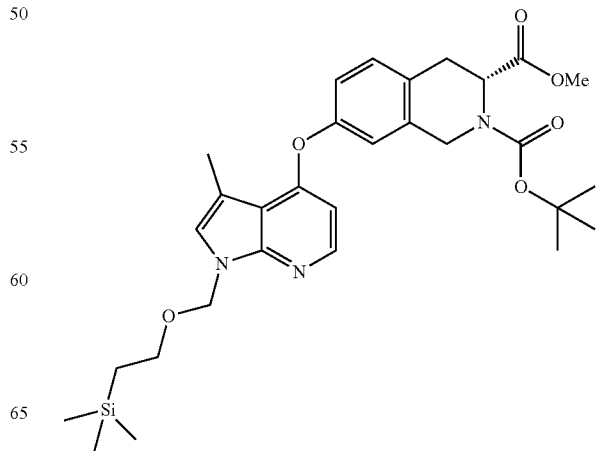

2-(tert-Butyl) 3-methyl (R)-7-((3-methyl-1-((2-(trimethylsilyl)ethoxy)methyl)-1H-pyrrolo[2,3-b]pyridin-4-yl)oxy)-3,4-dihydroisoquinoline-2,3(1H)-dicarboxylate (Intermediate 39B)

Intermediate 39B was prepared from intermediates 1A-a and intermediate 39A using a similar procedure to that used to prepare intermediate 36C.

LCMS (Method 3): Rt=1.93 min, m/z 568.3 [M+H]⁺

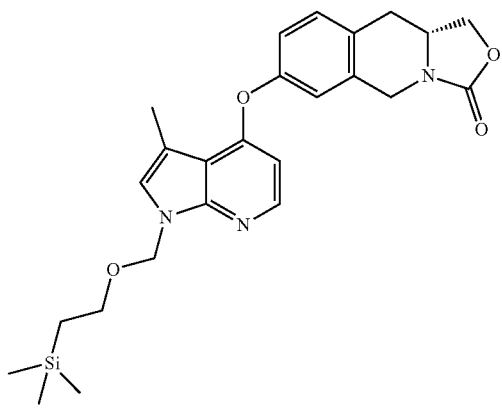 [SMILES: Cc1cn(COCC[Si](C)(C)C)c2nccc(Oc3ccc4c(c3)CN3C(=O)OC[C@H]3C4)c12]

(R)-7-((3-Methyl-1-((2-(trimethylsilyl)ethoxy)methyl)-1H-pyrrolo[2,3-b]pyridin-4-yl)oxy)-1,5,10,10a-tetrahydro-3H-oxazolo[3,4-b]isoquinolin-3-one (Intermediate 39C)

Intermediate 39B (353 mg, 0.62 mmol) was dissolved in THF (20 mL) and sodium borohydride (94 mg, 2.49 mmol) was added. The reaction mixture was stirred at 50° C. overnight. After quenching with acetic acid (0.5 mL), water was added and the product was extracted into ethyl acetate. The extract was dried (Na₂SO₄) and evaporated. The title compound was obtained as a colourless oil (344 mg).

LCMS (Method 3): Rt=1.68 min. m/z 466.3 [M+H]⁺

Step D

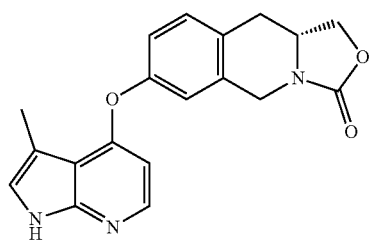 [SMILES: Cc1c[nH]c2nccc(Oc3ccc4c(c3)CN3C(=O)OC[C@H]3C4)c12]

(R)-7-((3-methyl-1H-pyrrolo[2,3-b]pyridin-4-yl)oxy)-1,5,10,10a-tetrahydro-3H-oxazolo[3,4-b]isoquinolin-3-one (Intermediate 39D)

Intermediate 39D was prepared from intermediate 39C using a procedure analogous to that used in the preparation of example 1, step C.

LCMS (Method 1): Rt=2.88 min, m/z 336.2 [M+H]⁺

Step E

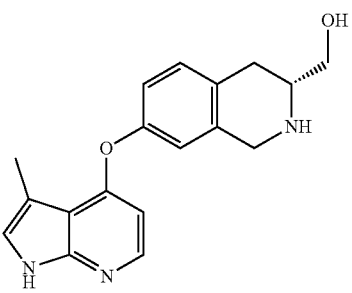 [SMILES: Cc1c[nH]c2nccc(Oc3ccc4c(c3)CN[C@@H](CO)C4)c12]

(R)-(7-((3-Methyl-1H-pyrrolo[2,3-b]pyridin-4-yl)oxy)-1,2,3,4-tetrahydroisoquinolin-3-yl)methanol (Example 39)

Intermediate 39D (195 mg, 5.82 mmol) was dissolved in THF (10 mL) and 6N sodium hydroxide (10 mL) was added. The reaction was stirred at 100° C. for 2 days. After allowing to cool the mixture was partitioned between ethyl acetate and water. The aqueous phase was acidified and extracted again with ethyl acetate. The combined organic were dried (Na₂SO₄) and evaporated. The crude product was purified by MDAP (basic) to give a white solid.

LCMS (Method 1): Rt=1.84 min, m/z 310.2 [M+H]⁺
¹H NMR (400 MHz, d6-DMSO) δ 11.32 (s, 1H), 7.98 (d, J=5.4 Hz, 1H), 7.15 (d, J=8.7 Hz, 1H), 7.12-7.09 (m, 1H), 6.92-6.83 (m, 2H), 6.23 (d, J=5.4 Hz, 1H), 4.72-4.66 (m, 1H), 3.96-3.82 (m, 2H), 3.51-3.36 (m, 2H), 2.87-2.79 (m, 1H), 2.68 (dd, J=4.4, 16.1 Hz, 1H), 2.41 (dd, J=10.8, 16.0 Hz, 1H), 2.33 (d, J=0.9 Hz, 3H), 2.33-2.29 (m, 1H).

The following racemic compound was resolved using the conditions given below to give the pure enantiomers.

| Racemate | Separation | Analysis | 1st eluting | 2nd eluting |
|---|---|---|---|---|
| Example 18 | MD SFC YMC Amylose-SA 55/45 IPA (0.1% DEA)/CO₂ 70 mL/min 40° C. 275 nM; column dimensions 250 × 20 mm, 5 µm | MD SFC YMC Amylose-C 55/45 IPA (0.1% DEA)/CO₂ 0.95 mL/min 40° C.; column dimensions 150 × 2.0 mm, 5 µm | Example 18A Rt = 0.9 mins | Example 18B Rt = 1.4 mins |

Pharmacological Activity of the Compounds of the Invention

In Vitro Inhibitory Activity Assay Description

The effectiveness of compounds of the invention to inhibit Rho kinase activity can be determined in a 10p assay containing 40 mM Tris pH7.5, 20 mM MgC₂ 0.1 mg/ml BSA, 50 µM DTT and 2.5 µM peptide substrate (Myelin Basic Protein) using an ADP-Glo kit (Promega). Compounds were dissolved in DMSO such that the final concentration of DMSO was 1% in the assay. All reactions/incubations are performed at 25° C. Compound (2 ul) and either Rho kinase 1 or 2 (4 µl) were mixed and incubated for 30 mins. Reactions were initiated by addition of ATP (4 µl) such that the final concentration of ATP in the assay was 10 µM. After a 1 hour incubation 10 µl of ADP-Glo Reagent was added and after a further 45 minute incubation 20 ul of Kinase Detection Buffer was added and the mixture incubated for a further 30 minutes. The luminescent signal was measured on a luminometer. Controls consisted of assay wells that did not contain compound with background determined using assay wells with no enzyme added. Compounds were tested in dose-response format and the inhibition of kinase activity was calculated at each concentration of compound. To determine the $IC_{50}$ (concentration of compound required to inhibit 50% of the enzyme activity) data were fit to a plot of % inhibition vs $Log_{10}$ compound concentration using a sigmoidal fit with a variable slope and fixing the maximum to 100% and the minimum to 0%. To determine the Ki values the Cheng-Prusoff equation was utilized ($Ki=IC_{50}/(1+[S]/Km)$)

Compounds according to the invention showed Ki values lower than 5 µM and for most of the compounds of the invention Ki is even lower that 500 nM.

The results for individual compounds are provided below in Table 4 and are expressed as range of activity.

TABLE 4

| Example | Activity ROCK1 | Activity ROCK2 |
|---|---|---|
| 1 | +++ | +++ |
| 2 | +++ | +++ |
| 3 | ++ | ++ |
| 4 | ++ | ++ |
| 5 | +++ | +++ |
| 6 | ++ | ++ |
| 7 | + | + |
| 8 | + | + |
| 9 | + | + |
| 10 | +++ | +++ |
| 11 | ++ | ++ |
| 12 | +++ | +++ |
| 13 | ++ | ++ |
| 14 | ++ | +++ |
| 15 | ++ | ++ |
| 16 | ++ | +++ |
| 17 | ++ | +++ |
| 18 | ++ | ++ |
| 19 | +++ | +++ |
| 20 | +++ | +++ |
| 21 | ++ | +++ |
| 22 | ++ | ++ |
| 23 | +++ | +++ |
| 24 | ++ | +++ |
| 25 | ++ | +++ |
| 26 | ++ | ++ |
| 27 | + | + |
| 28 | ++ | ++ |
| 29 | ++ | ++ |
| 30 | ++ | ++ |
| 31 | ++ | ++ |
| 32 | ++ | ++ |
| 33 | + | ++ |
| 34 | +++ | +++ |
| 35 | ++ | +++ |
| 36 | +++ | +++ |
| 37 | +++ | +++ |
| 38 | ++ | +++ |
| 39 | +++ | +++ |
| 18A | ++ | +++ |
| 18B | ++ | ++ | wherein the compounds are classified in term of potency with respect to their inhibitory activity on ROCK 1 ROCK 2 isoforms according to the following classification criterion:

+++: Ki<5 nM

++: Ki in the range 5-50 nM

+: Ki>50 nM.

The invention claimed is:

1. A compound of formula (I)

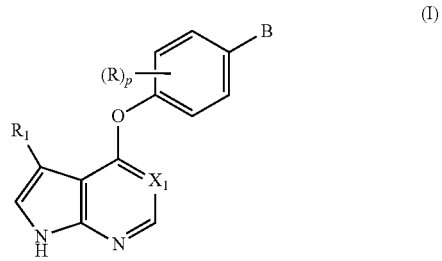

wherein $X_1$ is a carbon or a nitrogen atom;

p is zero or an integer from 1 to 3;

each R, when present, is H or halogen;

$R_1$ is —H, —CN or ($C_1$-$C_6$) alkyl;

B is ($C_3$-$C_8$)heterocycloalkyl, or

B is a group of formula $R_2R_3N$—($C_1$-$C_6$) alkyl, optionally substituted by one or more substituents selected from hydroxyl, ($C_1$-$C_6$) alkyl, ($C_1$-$C_6$) hydroxyalkyl, ($C_1$-$C_6$) alkoxycarbonyl, ($C_3$-$C_{10}$) cycloalkoxycarbonyl, aryl ($C_1$-$C_6$) alkoxycarbonyl;

wherein $R_2$ and $R_3$, the same or different, are selected from the group consisting of

—H, ($C_1$-$C_6$) alkyl, ($C_1$-$C_6$) hydroxyalkyl, ($C_3$-$C_8$)heterocycloalkyl, further optionally substituted by one or more ($C_1$-$C_6$) alkyl;

or

B is a group of formula $R_2R_3N$—($C_1$-$C_6$) alkyl, optionally substituted by one or more substituents selected from hydroxyl, ($C_1$-$C_6$) alkyl, ($C_1$-$C_6$) hydroxyalkyl, ($C_1$-$C_6$) alkoxycarbonyl, ($C_3$-$C_{10}$) cycloalkoxycarbonyl, aryl ($C_1$-$C_6$) alkoxycarbonyl;

wherein $R_2$ and $R_3$, taken together with the nitrogen atom they are linked to, form a heterocyclic ring, preferably a 4 to 6 membered mono-cyclic saturated heterocyclic ring, wherein at least one further ring carbon atom is optionally replaced by at least one further group independently selected from N, NH, S or O and/or may bear an -oxo (=O) substituent group, said heterocyclic ring is further optionally including spiro disubstitution; and said heterocyclic ring in its turn is further optionally substituted by one or more substituents selected from hydroxyl, ($C_1$-$C_6$) alkyl, ($C_1$-$C_6$) hydroxyalkyl, ($C_1$-$C_6$) alkoxycarbonyl, ($C_3$-$C_{10}$) cycloalkoxycarbonyl, Aryl ($C_1$-$C_6$) alkoxycarbonyl;

or

B is a group of formula $R_2R_3N$—($C_1$-$C_6$) alkyl, optionally substituted by one or more substituents selected from hydroxyl, ($C_1$-$C_6$) alkyl, ($C_1$-$C_6$) hydroxyalkyl, ($C_1$-$C_6$) alkoxycarbonyl, ($C_3$-$C_{10}$) cycloalkoxycarbonyl, aryl ($C_1$-$C_6$) alkoxycarbonyl;

wherein $R_3$ is selected from the group consisting of

—H, ($C_1$-$C_6$) alkyl, ($C_1$-$C_6$) hydroxyalkyl, (C$_3$-C$_8$) heterocycloalkyl, further optionally substituted by one or more (C$_1$-C$_6$) alkyl;

R$_2$ is a divalent group —(CH$_2$)$_q$—, wherein q is an integer from 1 to 3; said divalent group being connected to the carbon atom in ortho position on the adjacent phenyl ring to form a heterocyclic ring, preferably a 4 to 10 membered heterocyclic ring fused with the phenyl ring; said heterocyclic ring being optionally in its turn further substituted with one or more group selected from (C$_1$-C$_6$) alkyl, (C$_1$-C$_6$) hydroxyalkyl;

or

B is a divalent group —(CH$_2$)$_s$—, wherein s is an integer from 2 to 8, said divalent group being connected to the adjacent carbon in ortho position on the phenyl ring to form a fused ring; preferably a 4 to 10 membered monocyclic ring fused with the phenyl ring; said ring being further substituted with one or more —NH$_2$;

and pharmaceutically acceptable salts and solvates thereof.

2. A compound according to claim 1 wherein each of X$_1$ is a carbon atom;
represented by formula Ia:

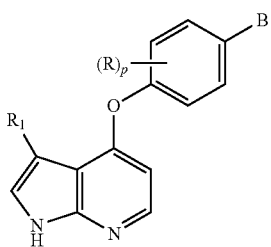

Ia and R, R$_1$, B and p, are as in claim 1.

3. A compound according to claim 1 wherein
X$_1$ is a carbon or a nitrogen atom;
p is zero or an integer from 1 or 2;
each R, when present, is H or a halogen;
R$_1$ is —H or (C$_1$-C$_6$) alkyl;
B is a group R$_2$R$_3$N—(C$_1$-C$_6$) alkyl, said alkyl being optionally substituted by one or more substituents selected from (C$_1$-C$_6$) alkyl and/or (C$_1$-C$_6$) hydroxyalkyl;
wherein
R$_2$ and R$_3$, the same or different, are selected from the group consisting of
—H,
(C$_1$-C$_6$) alkyl,
(C$_1$-C$_6$) hydroxyalkyl,
(C$_3$-C$_8$) heterocycloalkyl, further optionally substituted by one or more (C$_1$-C$_6$) alkyl;
or
R$_2$ and R$_3$, taken together with the nitrogen atom they are linked to, form a morpholinyl, 2,7-diazaspiro[4,4]nonan-2-yl or piperazinyl ring
further optionally substituted with one or more methyl;
and pharmaceutically acceptable salts and solvates thereof.

4. A compound according to claim 1 wherein
X$_1$ is a ring carbon atom;
p is zero or an integer from 1 to 3;
each R, when present, is H or a halogen;
R$_1$ is H, —CN or methyl;
B is a (C$_3$-C$_8$)heterocycloalkyl selected from a1, a2 or a3:

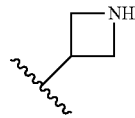 a1

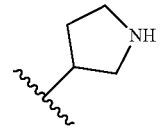 a2

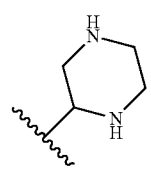 a3 or

B is a group of formula R$_2$R$_3$N—(C$_1$-C$_6$) alkyl, optionally substituted by one or more substituents selected from hydroxyl, (C$_1$-C$_6$) alkyl, (C$_1$-C$_6$) hydroxyalkyl, (C$_1$-C$_6$) alkoxycarbonyl, (C$_3$-C$_{10}$) cycloalkoxycarbonyl, aryl (C$_1$-C$_6$) alkoxycarbonyl;

wherein
R$_3$ is selected from the group consisting of
—H,
(C$_1$-C$_6$) alkyl,
(C$_1$-C$_6$) hydroxyalkyl,
(C$_3$-C$_8$)heterocycloalkyl, further optionally substituted by one or more (C$_1$-C$_6$) alkyl;

R$_2$ is a divalent group —(CH$_2$)$_q$—, q is an integer from 1 to 3, said divalent group being connected to the carbon atom in ortho position on the adjacent phenyl ring to form a heterobicyclic ring of formula a4, a5, a6, a7 or a8

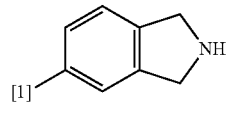 a4

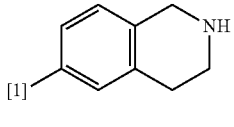 a5

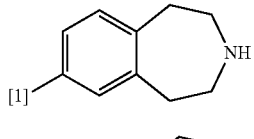 a6

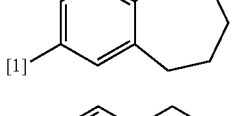 a7

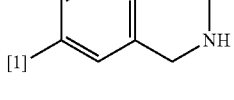 a8 wherein [1] represent the point of attachment of the heterobicyclic ring to the rest of the molecule via the ether bridge, and said heterobicyclic ring being optionally in its turn further substituted with one or more $(C_1-C_6)$ alkyl and/or $(C_1-C_6)$ hydroxyalkyl group;

and pharmaceutically acceptable salts and solvates thereof.

5. A compound according to claim 1 wherein $X_1$ is a carbon ring atom;

p is zero or an integer from 1 to 3;

each R, when present, is H or halogen;

$R_1$ is methyl;

B is a divalent group —$(CH_2)_s$—, wherein s is an integer from 2 to 8, said divalent group being connected to the carbon atom in ortho position of the same phenyl ring to form a bicyclic hydrocarbon ring selected from b1 or b2:

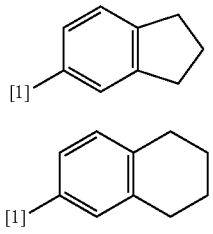

wherein [1] represents the point of attachment of the heterobicyclic ring to the rest of the molecule via the ether bridge, and said bicyclic hydrocarbon ring is further substituted with one or more —$NH_2$;

and pharmaceutically acceptable salts and solvates thereof.

6. A compound according to claim 1, wherein $X_1$ is a carbon or a nitrogen ring atom;

p is zero or an integer from 1 to 3;

each R, when present, is fluoro;

$R_1$ is —H, —CN or methyl,

B is a azetidinyl (a1), pyrrolidinyl (a2) or piperazinyl (a3) ring;

or

B is a group $R_2R_3N$—$(C_1-C_6)$ alkyl, the —$(C_1-C_6)$ alkyl being optionally substituted by one or more substituents selected from hydroxyl, methyl, hydroxymethyl and cyclopropyl;

wherein $R_2$ and $R_3$, the same or different, are selected from the group consisting of

—H,

-methyl

-hydroxyethyl

-pyranyl, piperidinyl, further optionally substituted by one or more methyl;

or $R_2$ and $R_3$, taken together with the nitrogen atom they are linked to, form a pyrrolidinyl, morpholinyl, 2,7-diazaspiro[4,4]nonan-2-yl or 4-methylpiperazin-1-yl ring;

or $R_3$ is selected from the group consisting of:

—H,

-methyl; and $R_2$ is connected to the carbon atom in ortho position on the adjacent phenyl ring to form a heterobicyclic ring selected from 5-methylisoindoline (a4), 6-methyl-1,2,3,4-tetrahydroisoquinoline (a5), 7-methyl-2,3,4,5-tetrahydro-1H-benzo[c]azepine (a6) and 7-methyl-2,3,4,5-tetrahydro-1H-benzo[d]azepine (a7) and 7-methyl-1,2,3,4-tetrahydroisoquinoline (a8);

said heterocyclic ring being optionally in its turn further substituted with one or more methyl and/or hydroxymethyl groups;

or

B is a bicyclic hydrocarbon ring selected from 2,3-dihydro-1H-indene-5yl (b1) and 1,2,3,4-tetrahydronaphthalene-6yl (b2);

said bicyclic hydrocarbon ring being further optionally in its turn substituted with one or more —$NH_2$;

and pharmaceutically acceptable salts and solvates thereof.

7. A compound according to claim 1 selected from:

7-((3-methyl-1H-pyrrolo[2,3-b]pyridin-4-yl)oxy)-1,2,3,4-tetrahydroisoquinoline;

4-(isoindolin-5-yloxy)-3-methyl-1H-pyrrolo[2,3-b]pyridine;

N-methyl-1-(4-((3-methyl-1H-pyrrolo[2,3-b]pyridin-4-yl)oxy)phenyl)methanamine;

2-(4-((1H-pyrrolo[2,3-b]pyridin-4-yl)oxy)phenyl)ethanamine;

7-((3-methyl-1H-pyrrolo[2,3-b]pyridin-4-yl)oxy)-2,3,4,5-tetrahydro-1H-benzo[d]azepine;

7-((5-methyl-7H-pyrrolo[2,3-d]pyrimidin-4-yl)oxy)-1,2,3,4-tetrahydroisoquinoline;

5-methyl-4-(4-(pyrrolidin-3-yl)phenoxy)-7H-pyrrolo[2,3-d]pyrimidine;

2-(4-((5-methyl-7H-pyrrolo[2,3-d]pyrimidin-4-yl)oxy)phenyl)ethanamine;

(4-((5-methyl-7H-pyrrolo[2,3-d]pyrimidin-4-yl)oxy)phenyl)methanamine;

2-methyl-7-((3-methyl-1H-pyrrolo[2,3-b]pyridin-4-yl)oxy)-1,2,3,4-tetrahydroisoquinoline;

6-((3-methyl-1H-pyrrolo[2,3-b]pyridin-4-yl)oxy)-1,2,3,4-tetrahydroisoquinoline;

(3-fluoro-4-((3-methyl-1H-pyrrolo[2,3-b]pyridin-4-yl)oxy)phenyl)methanamine;

3-methyl-4-(4-(piperazin-2-yl)phenoxy)-1H-pyrrolo[2,3-b]pyridine;

5-((3-methyl-1H-pyrrolo[2,3-b]pyridin-4-yl)oxy)-2,3-dihydro-1H-inden-2-amine;

7-((3-methyl-1H-pyrrolo[2,3-b]pyridin-4-yl)oxy)-2,3,4,5-tetrahydro-1H-benzo[c]azepine;

8-((3-methyl-1H-pyrrolo[2,3-b]pyridin-4-yl)oxy)-2,3,4,5-tetrahydro-1H-benzo[c]azepine;

4-(4-(azetidin-3-yl)phenoxy)-3-methyl-1H-pyrrolo[2,3-b]pyridine;

3-methyl-4-(4-(pyrrolidin-2-yl)phenoxy)-1H-pyrrolo[2,3-b]pyridine;

2-(4-((3-methyl-1H-pyrrolo[2,3-b]pyridin-4-yl)oxy)phenyl)ethanamine;

3-methyl-4-(4-(pyrrolidin-3-yl)phenoxy)-1H-pyrrolo[2,3-b]pyridine;

(4-((3-methyl-1H-pyrrolo[2,3-b]pyridin-4-yl)oxy)phenyl)methanamine;

3-methyl-4-(4-(2-(pyrrolidin-1-yl)ethyl)phenoxy)-1H-pyrrolo[2,3-b]pyridine;

1-(3-fluoro-4-((3-methyl-1H-pyrrolo[2,3-b]pyridin-4-yl)oxy)phenyl)ethanamine;

1-(4-((3-methyl-1H-pyrrolo[2,3-b]pyridin-4-yl)oxy)phenyl)ethanamine;

2-(4-((3-methyl-1H-pyrrolo[2,3-b]pyridin-4-yl)oxy)phenyl)propan-2-amine;
6-((3-methyl-1H-pyrrolo[2,3-b]pyridin-4-yl)oxy)-1,2,3,4-tetrahydronaphthalen-1-amine;
4-(4-((3-methyl-1H-pyrrolo[2,3-b]pyridin-4-yl)oxy)benzyl)morpholine;
N-(4-((3-methyl-1H-pyrrolo[2,3-b]pyridin-4-yl)oxy)benzyl)tetrahydro-2H-pyran-4-amine;
N,N-dimethyl-1-(44(3-methyl-1H-pyrrolo[2,3-b]pyridin-4-yl)oxy)phenyl)methanamine;
1-methyl-N-(4-((3-methyl-1H-pyrrolo[2,3-b]pyridin-4-yl)oxy)benzyl)piperidin-4-amine;
2-((4-((3-methyl-1H-pyrrolo[2,3-b]pyridin-4-yl)oxy)benzyl)amino)ethanol;
4-(4-(2,7-diazaspiro[4.4]nonan-2-ylmethyl)phenoxy)-3-methyl-1H-pyrrolo[2,3-b]pyridine;
3-methyl-4-(4-((4-methylpiperazin-1-yl)methyl)phenoxy)-1H-pyrrolo[2,3-b]pyridine;
4-((1,2,3,4-tetrahydroisoquinolin-7-yl)oxy)-1H-pyrrolo[2,3-b]pyridine-3-carbonitrile;
(4-((1H-pyrrolo[2,3-b]pyridin-4-yl)oxy)-3,5-difluorophenyl)methanamine;
(S)-2-amino-3-(3-fluoro-4-((3-methyl-1H-pyrrolo[2,3-b]pyridin-4-yl)oxy)phenyl)propan-1-ol;
(S)-2-amino-3-(4-((3-methyl-1H-pyrrolo[2,3-b]pyridin-4-yl)oxy)phenyl)propan-1-ol;
2-amino-2-(4-((3-methyl-1H-pyrrolo[2,3-b]pyridin-4-yl)oxy)phenyl)ethanol;
(R)-(7-((3-methyl-1H-pyrrolo[2,3-b]pyridin-4-yl)oxy)-1,2,3,4-tetrahydroisoquinolin-3-yl)methanol;
First Eluted enantiomer of 3-methyl-4-(4-(pyrrolidin-2-yl)phenoxy)-1H-pyrrolo[2,3-b]pyridine;
Second Eluted enantiomer of 3-methyl-4-(4-(pyrrolidin-2-yl)phenoxy)-1H-pyrrolo[2,3-b]pyridine
or pharmaceutically acceptable salts and solvates thereof.

8. A pharmaceutical composition comprising a compound as defined in claim 1, or a pharmaceutically acceptable salt thereof in admixture with one or more pharmaceutically acceptable carrier or excipient.

9. A pharmaceutical composition according to claim 8 suitable to be administered by inhalation, such as inhalable powders, propellant-containing metering aerosols or propellant-free inhalable formulations.

10. A compound as defined in claim 1, in combination with one or more active ingredients selected from the classes consisting of organic nitrates and NO donors; inhaled NO; stimulator of soluble guanylate cyclase (sGC); prostaciclin analogue PGI2 and agonist of prostacyclin receptors; compounds that inhibit the degradation of cyclic guanosine monophosphate (cGMP) and/or cyclic adenosine monophosphate (cAMP); human neutrophilic elastase inhibitors; compounds inhibiting the signal transduction cascade; active substances for lowering blood pressure; neutral endopeptidase inhibitors; osmotic agents; ENaC blockers; anti-inflammatories including corticosteroids and antagonists of chemokine receptors; bronchodilators; antihistamine drugs; anti-tussive drugs; antibiotics and DNase drug substance and selective cleavage agents; agents that inhibit ALK5 and/or ALK4 phosphorylation of Smad2 and Smad3; tryptophan hydroylase 1 (TPH1) inhibitors and multi-kinase inhibitors.

11. A device comprising the pharmaceutical composition according to claim 8, which may be a single- or multi-dose dry powder inhaler, a metered dose inhaler, or a soft mist nebulizer.

12. A pharmaceutical composition comprising a compound as defined in claim 7, or a pharmaceutically acceptable salt thereof, either alone or in combination with another one or more active ingredients, in admixture with one or more pharmaceutically acceptable carriers or excipients.

13. The pharmaceutical composition according to claim 12 suitable to be administered by inhalation, such as inhalable powders, propellant-containing metering aerosols or propellant-free inhalable formulations.

14. A compound as defined in claim 7, in combination with one or more active ingredients selected from the classes consisting of organic nitrates and NO donors; inhaled NO; stimulator of soluble guanylate cyclase (sGC); prostaciclin analogue PGI2 and agonist of prostacyclin receptors; compounds that inhibit the degradation of cyclic guanosine monophosphate (cGMP) and/or cyclic adenosine monophosphate (cAMP); human neutrophilic elastase inhibitors; compounds inhibiting the signal transduction cascade; active substances for lowering blood pressure; neutral endopeptidase inhibitors; osmotic agents; ENaC blockers; anti-inflammatories including corticosteroids and antagonists of chemokine receptors; bronchodilators; antihistamine drugs; anti-tussive drugs; antibiotics and DNase drug substance and selective cleavage agents; agents that inhibit ALK5 and/or ALK4 phosphorylation of Smad2 and Smad3; tryptophan hydroylase 1 (TPH1) inhibitors and multi-kinase inhibitors.

15. A device comprising the pharmaceutical composition according to claim 12, which may be a single- or multi-dose dry powder inhaler, a metered dose inhaler, or a soft mist nebulizer.

* * * * *